United States Patent [19]

Wahleithner et al.

[11] Patent Number: 5,480,801
[45] Date of Patent: Jan. 2, 1996

[54] **PURIFIED PH NEUTRAL *RHIZOCTONIA LACCASES* AND NUCLEIC ACIDS ENCODING SAME**

[75] Inventors: Jill A. Wahleithner, Davis, Calif.; Bjoern E. Christensen, Holte; Palle Schneider, Ballerup, both of Denmark

[73] Assignee: Novo Nordisk A/S, Bagsvaerd, Denmark

[21] Appl. No.: 172,331

[22] Filed: Dec. 22, 1993

Related U.S. Application Data

[63] Continuation-in-part of Ser. No. 122,230, Sep. 17, 1993, abandoned, Ser. No. 122,827, Sep. 17, 1993, abandoned, and Ser. No. 162,827, Dec. 3, 1993, abandoned.

[51] Int. Cl.$^6$ .............................. C12N 5/14; C12N 5/16; C12N 15/31; C12N 15/52
[52] U.S. Cl. .................. 435/254.3; 536/23.2; 435/320.1; 435/254.2; 435/254.21; 435/252.3; 435/252.31; 435/257.33; 435/240.2; 435/240.4
[58] Field of Search .......................... 536/23.1; 435/69.1, 435/69.2, 172.3, 252.3, 254.11, 254.3, 320.1, 189

[56] References Cited

U.S. PATENT DOCUMENTS 5,252,726  10/1993  Woldike .................. 536/24.1

FOREIGN PATENT DOCUMENTS

| | | |
|---|---|---|
| 0408803A1 | 1/1991 | European Pat. Off. . |
| 0429422A1 | 5/1991 | European Pat. Off. . |
| 0433258A1 | 6/1991 | European Pat. Off. . |
| 0504005A1 | 9/1992 | France . |
| 0060467A1 | 3/1982 | Germany . |
| 3037992A1 | 8/1982 | Germany . |
| 9201046 | 1/1992 | WIPO . |
| WO92/16633 | 10/1992 | WIPO . |

OTHER PUBLICATIONS

Hanks et al Science vol. 241 pp. 42–52 Jul. 1, 1988.
Bullag et al Appl. Envir. Micro. 48(4) 849–54 1984.
Lee et al. Science vol. 239 pp. 1288 1988.
Leonowicz et al., Chem Abstracts, vol. 100, pp. 230–231, 1984.

*Primary Examiner*—Mindy B. Fleisher
*Assistant Examiner*—David B. Schmickel
*Attorney, Agent, or Firm*—Steve T. Zelson; Karen A. Lowney

[57] ABSTRACT

The present invention relates to isolated nucleic acid fragments containing a sequence encoding a *Rhizoctonia solani* laccase having optimum activity at a neutral or basic pH. and the laccase proteins encoded thereby.

30 Claims, 21 Drawing Sheets

```
  1 AGCGTCACCAGACATCGGATGAAAACGGAAAGTGTATGGCCATTTGACGTCTGCGGC           60
 61 AACCACTGTTCATCTCGCGAGCTAAACATGGGCGACGTATAAGAAGAACGCGAGAATGGGC      120
121 AGATTTCGATATCCCCTCTCGGTTTTGGTCTGCCTGCTTCGGCTTGCGGCGCAC             180
                                                M  A  R  T             4
181 CACTTTCCTTGTCTCCTCTTGTTTCCGCTCTGTTCTTGCGCACCGTGAGTA                240
     T  F  L  V  S  S  L  F  V  S  A  V  L  A  R  T  V  E  Y           24
241 CGGCTTGAAGATTAGTGATGGGGAGATAGCTCCTGACGGTGTTAAGCGTAATGCGACTTT      300
     G  L  K  I  S  D  G  E  I  A  P  D  G  V  K  R  N  A  T  L       44
301 GGgtacgcactccctgtaatccaacaattcaaggtttctgatgctcttggtcagTAAATGGA    360
                                                           V  N  G    47
361 GGGTATCCCGGTTCCACTCATTTTGCCAACAAGGGGGATACTCTCAAAGTCAAGGTCAA       420
     G  Y  P  G  P  L  I  F  A  N  K  G  D  T  L  K  V  K  V  Q       67
421 AACAAGCTCACGAATCCTGAGATGTATCGCACCACTTCCATCgtatgttcgttcgatatc      480
     N  K  L  T  N  P  E  M  Y  R  T  T  S  I                         81
481 tactaatacatccgtcgctaaatatcttgtagCATTGGCACGGTCTCTTACAACATAGAA     540
                                     H  W  H  G  L  L  Q  H  R         90
```

FIG. 1A

```
541  ACGCCGACGACGACGGTCCTTCGTTCGTCACTCAGgtaggattctggaaggttggccctga   600
 90   N   A   D   D   D   G   P   S   F   V   T   Q                 102

601  actctctgttaaccgacaacccgatgtcaccagTGCCCGATTGTTCCACGCGAGTCGTAT    660
102                                   C   P   I   V   P   R   E   S   Y  111

661  ACTTACACCATACCCTCTGGACGATCAAACCGGAACCTATTGGTACCATAGCCACTGAGT    720
111   T   Y   T   I   P   L   D   D   Q   T   G   T   Y   W   Y   H   S   H   L   S  131

721  TCGCAATACGTTGATGGTCTTCGAGGCCCGCTGGTAATCTgtgagtatcttgacttgtct    780
131   S   Q   Y   V   D   G   L   R   G   P   L   V   I                 144

781  actgaaggcaacgagactaaaacaagcgtcgattcacagATGgttcgtctcccctttatt   840
144                                           Y                        145

841  tagctctctggatctcattctcacgtaatacatgatagATCCCAAGGATCCTCACAGGCG    900
144                                         D   P   K   D   P   H   R   R  152

901  TTTGTATGATGTTGACGATGAGAAGACCGTCCTGATCATCGGTGACTGGTATCATGAATC    960
152   L   Y   D   V   D   D   E   K   T   V   L   I   I   G   D   W   Y   H   E   S  172

961  GTCCAAGGCAATCCTTGCTTCTGGTAACATTACCCGACAGtaagtgatacatgccggtcc   1020
172   S   K   A   I   L   A   S   G   N   I   T   R   Q                 185
```

FIG. 1B

```
1021  cagaaaattctctaaatttcattacagGCGACCGGTCTCTGCCACCATCAACGG  1080
                                R  P  V  S  A  T  I  N  G   194

1081  CAAAGGTCGATTTGACCCTGCCAACACTCCTGCCAACTACTCTGTACACCCTCAA  1140
       K  G  R  F  D  P  D  N  T  P  A  N  P  D  T  L  Y  T  L  K   214

1141  GGTCAAGCGAGGGAAGCGCTATCGTCTCCGTGTCATCAATAGCTCGGAGATCGCTTCGTT  1200
       V  K  R  G  K  R  Y  R  L  R  V  I  N  S  S  E  I  A  S  F   234

1201  CCGATTCAGTCTGTGGAAGGTCACAAGGTGACTGTGATTGCTGCCGATGGCGTCTCTACCAA  1260
       R  F  S  V  E  G  H  K  V  T  V  I  A  A  D  G  V  S  T  K   254

1261  ACCGTATCAGGTCGATGCGTTTGATATTCTAGCAGGACAGCGCATAGATTGCGTCgtaag  1320
       P  Y  Q  V  D  A  F  D  I  L  A  G  Q  R  I  D  C  V       272

1321  tgtcgtccgaacccacatctgagctcaagtgttgatacatgcgcgtttatagGTGGAGGC  1380
                                                            V  E  A   275

1381  GAACCAAGAACCCGACACATACTGGATCAACGCTCCACCGTCTGACCAACGTGCCCAACAAGAC  1440
       N  Q  E  P  D  T  Y  W  I  N  A  P  L  T  N  V  P  N  K  T   295

1441  CGCTCAGGCTCTCCTGGTTTATGAGGAGGATCGTCGGCCTTACCACCCTCCAAAGGGCCC  1500
       A  Q  A  L  L  V  Y  E  E  D  R  R  P  Y  H  P  P  K  G  P   315

1501  GTATCGCAAGTGGAGCGTCTCTGAGGCGATCATCAAGTACTGGAATCACAAGCACAAGCA  1560
       Y  R  K  W  S  V  S  E  A  I  I  K  Y  W  N  H  K  H  K  H   335
```

FIG. 1C

```
1561  CGGACGTGGTTGCTGTCTGGAGACATGGAGGCTCGAAGGCTCGGATGATCGAGGGTAGCCA  1620
335    G  R  G  L  L  S  G  H  G  G  G  L  K  A  R  M  I  E  G  S  H   340

1621  TCATCTGCATTCGCGGCCAGCGTCGTTAAGCGCCAGAATGAGACCACCACTGTTGTAATGGA 1680
340    H  L  H  S  R  S  V  V  K  R  Q  N  E  T  T  V  V  M  D        350

1681  CGAGAGCAAGCTCGTTgtaagtaccatatttaaagttggttgggtttcgaatacttatt   1740
350    E  S  K  L  V                                                  350

1741  tcaacttttcttagCCACTGGAATACCCCGGCTGCATGCGGGTCTAAACCTGCTGACC    1800
                    P  L  E  Y  P  G  A  A  C  G  S  K  P  A  D       365

1801  TCGTCTTGGATCTCACTTTTGGTTTGgtatgtagccaaatcgcccatatacaggatactg   1860
365    L  V  L  D  L  T  F  G  L                                     374

1861  aatattgtgttgtgcgtgtagAACTTTGCTACCGGGCACTGGATGATCAACGGTATCCCAT 1920
                          N  F  A  T  G  H  W  M  I  N  G  I  P       387

1921  ACGAGTCTCCCAAAATCCCCACATTGCTCAAGATCCTCACTGATGAGGACGGGGTTACCG   1980
387    Y  E  S  P  K  I  P  T  L  L  K  I  L  T  D  E  D  G  V  T    407

1981  AGTCTGACTTgtatgttcccttttcgtatcttcgtgtgactgactcgtgctggt         2040
407    E  S  D  F                                                    411

2041  gggaatttagCACCAAGGAGCACACAGTCATACTCCCGAAGAACAAATGCATCGAAT      2100
411             T  K  E  E  H  T  V  I  L  P  K  N  K  C  I  E       427
```

FIG. 1D

```
2101 TCAACATCAAGGGGAACTCGGGTATTCCCATTACGCACCCCGTACATCTTCACGGTgtaa    2160
 427  F  N  I  K  G  N  S  G  I  P  I  T  H  P  V  H  L  H  G         446

2161 gtgcatatcggatggttacgatactaaggctcatcaactttagCACACTTGGATGT         2220
 446                                             H  T  W  D  V        451

2221 CGTACAATTGGCAACAACCCACCCAATTATGTCAATCCTCCCCGTAGGACGTGGTTGG       2280
 451  V  Q  F  G  N  N  P  P  N  Y  V  N  P  P  R  R  D  V  V  G     471

2281 CTCTACAGATGCGGGTGTGAGGATTCAGTTCAAGACCGACAATCCAGGACCGTGGTTCCT     2340
 471  S  T  D  A  G  V  R  I  Q  F  K  T  D  N  P  G  P  W  F  L     491

2341 GCACTGgtgcgtgcgtcggtcccatcgtcgtatggttttctaatacgtccattctatt       2400
 491  H  C                                                            493

2401 tagCCATATTGACTGGCATCTTGAGGAGGGTTTCGCAAgtgagtactgagacctaagtgc     2460
 493    H  I  D  W  H  L  E  E  G  F  A                               504

2461 tactcggctcattactgattacgcatgtatgctctagTGGTGTTTGCTGAAGCGCCCG       2520
 504                                      M  V  F  A  E  A  P         511

2521 AAGCCGTCAAGGGAGGTCCAAAGAGCGTGGCCGTGGACTCTCAGTGGGAAGGGCTGTGTG     2580
 511  E  A  V  K  G  G  P  K  S  V  A  V  D  S  Q  W  E  G  L  C     531

2581 GCAAGTACGACAACTGGCTAAAATCAAATCCCGGCCAGCTGTAGGCGTATCGCAGCCACA     2640
 531  G  K  Y  D  N  W  L  K  S  N  P  G  Q  L  *                    545
```

FIG. 1E

```
2641  TTGGTGATGATTGAAAGTTGCATCTTGTTCCTATAACCGGCTCTTATATACGGGTGTCTC  2700
2701  CCAGTAAAGTCGTGTAGCCCAATTTCAGCCGAGACAGATATTTAGTGGACTCTTACTCTTGT  2760
2761  GTCCCATTGACGCACATCGTTGCATCAAACCTGCTTTTTATCGTCCCTCTTGTAATTTG  2820
2821  TGTTGCTGTAATGTATCG  2838
```

FIG. 1F

```
  1 AAGCTTCGGGCATGGATTGCATTTGTATTGT                                           180

181 AAACAAGTTACGAGAGAAAAACAATAGATCAGTTTTTGCCGAATCGGATGGCTTGAAACGGA            240

241 AGTACCGATGGCCGAGTCGAATGAATTAACGCATCTGAAACGGACCCTGAGTCG                    300

301 AGGCACCCCGCCCTTGGCCCGTATAAGTCACTGTCGCCAACTAGCACTTTTTCATTCC                360

361 CCCTTTCTTCCTCGTCTTCTCTTCTCTATGGCTCGGTCGACTACTTCACTCTTTG                   420
  1                                 M  A  R  S  T  T  S  L  F                 10

421 CACTGTCTCTGGCCGCACCGGCTTGGCTCGAGTCGTTGACTATGGGTTTGATGTGGCTA               480
 10  A  L  S  L  A  A  P  A  L  A  R  V  V  D  Y  G  F  D  V  A              30

481 ATGGGGCAGTGCTCCGGATGGTGTAACAAGGAACGCGGTTCTCGgtgagttagctgtaa               540
 30  N  G  A  V  A  P  D  G  V  T  R  N  A  V  L                             45

541 gatggtgtatgctggttgcctaacgggaatgtcagTCAATGGTCGCTTCCCTGGTCCA                600
 45                                    V  N  G  R  F  P  G  P                53

601 TTGATCACCGCCAACAAGGGGGATACACTTAAAATCACCGTGCGGAATAAACTCTCCGAT              660
 53  L  I  T  A  N  K  G  D  T  L  K  I  T  V  R  N  K  L  S  D              73
```

FIG. 2A

```
661  CCAACTATGCGAAGGAGCACGACCATCgttagtacttccctcatctgtcttgaaacttt    720
73    P  T  M  R  R  S  T  T  I                                    82

721  ctcatcttttgaagCACTGGCACGGTCTGCTCCAACACAGGACGGCAGAAGAAGATGG     780
82                 H  W  H  G  L  L  Q  H  R  T  A  E  E  D  G    97

781  CCCGGCCTTTGTAACCCAGgtatgcctctatcgtgctctgtccccgcgtccttcc         840
97    P  A  F  V  T  Q                                            103

841  ctgactcggggcgattctagTGCCCGATTCCTCCGCAAGAATCGTACACCTATACGATGCC  900
103                      C  P  I  P  P  Q  E  S  Y  T  Y  T  M  P 117

901  GCTCGGGCGAACAGACCGGCACGTATTGGTACCACAGCCACTTGAGCTCCCAGTATGTGGA  960
117   L  G  E  Q  T  G  T  Y  W  Y  H  S  H  L  S  S  Q  Y  V  D 137

961  CGGGTTGCGTGGGCCCATCGTTATTgtaagtcttcattaaccttattcttggctatgg    1020
137   G  L  R  G  P  I  V  I                                     145

1021 ctgattgtgacgtcgtggttagATGgttctgtggcttccacaagaagtcagcagcccttga 1080
145                         Y                                    145

1081 agctaacttattccagACCCCCGTACAGAAACTACTATGATGTCGACGACGA          1140
145                   D  P  H  D  P  Y  R  N  Y  Y  D  V  D  D  E 160

1141 GCGTACGGTCTTTACTTTAGCAGACTGGTACCACACGCCGTCGGAGGCTATCATTGCCAC  1200
160   R  T  V  F  T  L  A  D  W  Y  H  T  P  S  E  A  I  I  A  T 180
```

FIG. 2B

```
1201 CCACGATGTCTTGAAAACgtacgcgttaatccttctcttcctggtcacttt    1260
 180      H  D  V  L  K  T                                  185

1261 ctatcagGATCCCCGACTCGGGTACGATCAACGGCAAAGGCAAATACGATCCTGCTTCGG  1320
 185         I  P  D  S  G  T  I  N  G  K  G  K  Y  D  P  A  S   202

1321 CTAACACCAACAACGACACTCGAGAACCTCTACACTCTCAAAGTCAAAGTCAAACGGCAAGC  1380
 202  A  N  T  N  N  D  T  L  E  N  L  Y  T  L  K  V  K  R  G  K  222

1381 GGTATCGCCTGAGGATTATCAACGCCTCGGCCATCGCTTCGTTCCGGTTCGGGCGTGCAGG  1440
 222  R  Y  R  L  R  I  I  N  A  S  A  I  A  S  F  R  F  G  V  Q  242

1441 GCCACAAGTGCACGATCATCGAGGCTGATGGCGTCCTGACCAAACCGATCGAGGTCGATG   1500
 242  G  H  K  C  T  I  I  E  A  D  G  V  L  T  K  P  I  E  V  D  262

1501 CGTTTGATATTCTAGCAGGCCAGAGGTATAGCTGCATCgtaagtctacctatgccttgtt  1560
 262  A  F  D  I  L  A  G  Q  R  Y  S  C  I                       275

1561 gtgggagataagaacctgactgaatgtgctcccaatagTTGAAGGCCGACCAAGATCC    1620
 275                                        L  K  A  D  Q  D  P    282

1621 TGATTCCTACTGGATAAATGCGCCAATCACAAACGTTCTCAACACCAACGTCCAGGCATT  1680
 282  D  S  Y  W  I  N  A  P  I  T  N  V  L  N  T  N  V  Q  A  L  302

1681 GCTAGTGTATGAAGATGACAAGCGTCCTACTCACTACCCCTGGAAGCCGTTTTTGACATG  1740
 302  L  V  Y  E  D  D  K  R  P  T  H  Y  P  W  K  P  F  L  T  W  322
```

FIG. 2C

```
1741  GAAGATATCAAATGAAATCATTCAGTACTGGCAGCACAAGCACGGTCGCACGGTCACAA  1800
 322    K   I   S   N   E   I   I   Q   Y   W   Q   H   K   H   G   S   H   H   K   342

1801  GGGAAAGGGGCATCATCATAAAGTCCGGGCCATTGGAGGTGTATCCGGGTTGAGCTCCAG  1860
 342    G   K   G   H   H   H   K   V   R   A   I   G   G   V   S   G   L   S   S   R   362

1861  GGTTAAGAGACCGGGGCCGAGTTGGACGTCGAAGAAGGCTGTGCTGAGTTGGCTGCACTCGT  1920
 349    V   K   S   R   A   S   D   L   S   K   K   A   V   E   L   A   A   A   L   V   349

1921  TGCGGGTGAGGCCGAGTTGGACAAGAGGCAGAATGAGGATAATTCGACTATTGTATTGGA  1980
 349    A   G   E   A   E   L   D   K   R   Q   N   E   D   N   S   T   I   V   L   D   361

1981  TGAGACCAAGCTTATTgtaagtccccttaattttttcgtgtcacggaagctaacccgcg  2040
 361    E   T   K   L   I                                                                361

2041  taatagCCGTTGGTTCAACCTGGTGCAACGGGGCGCTCCAGACTGACGTCGTCGTGGTC  2100
 361                P   L   V   Q   P   G   A   P   G   G   S   R   P   A   D   V   V   V   379

2101  CCTCTGGACTTTGGCCCTgtatgtggctttcttgtattcgtccggaatgcaaactgatt  2160
 379    P   L   D   F   G   L                                                            385

2161  gggtgggctatagAACTTTGCCAACGGACTGTGGACGATAAACAATGTCCTACTCCCC  2220
 385                N   F   A   N   G   L   W   T   I   N   N   V   S   Y   S   P   401

2221  TCCGGATGTCCCTACTCTCCCTCAAGATCTTGACCGACAAAGACAAAGTCGACGCTTCTGA  2280
 401    P   D   V   P   T   L   L   K   I   L   T   D   K   D   K   V   D   A   S   D   421
```

FIG. 2D

```
2281 CTTgtaggttcctctcttctttcaaactagctactgacattaagtgaacgtcagCACG  2340
421  F                                                      T   423

2341 GCCGATGAACACACGTATATTCTTCCAAAGAACCAAGTTGTCGAGTTGCACATCAAGGA  2400
423  A D E H T Y I L P K N Q V V E L H I K G                      453

2401 CAGGCTTTGGGAATCGTACACCCCCTTCATCTGCATGGCgtacgtctttctcacactgtt  2460
453  Q A L G I V H P L H L H G                                    466

2461 ccagctcctattctctaacacactcctgcgatagCATGCCGTTCGACGTCGTCCAATTCGG  2520
466                                   H A F D V V Q F G           475

2521 CGACAACGCTCCAAACTACGTGAACTGTAGGGATGTAGTAGGCGTAACTGATGC  2580
475  D N A P N Y V N P P R R D V G V T D A                  495

2581 TGGAGTCCGTATCCAGTTCAGAACCGATAACCCGGCCCTTGGTTCCTCCATTGgtatgc  2640
495  G V R I Q F R T D N P G P W F L H C                         513

2641 tcttcatctcccaccgcttgtcttcttactttatgttttaccttgcgattagCCACATTGA  2700
513                                                      H I D   516

2701 TTGGCACTTGGAAGAAGGATTTGCTAgtaagttattattcctattccgaagcatcggggga  2760
516  W H L E E G F A                                              524

2761 gatgctaaccaagggtgtgtttaagTGGTATTCGCCGAAGCCTGAAGATATCAAGAA  2820
524                           M V F A E A P E D I K K         536
```

FIG. 2E

```
2821 AGGCTCTCAGAGTGTCAAGCCTGACGGACAATGGAAGAAACTATGCGAGAAGTATGAGAA 2880
 536  G  S  Q  S  V  K  P  D  G  Q  W  K  K  L  C  E  R  K  Y  E  K   556

2881 GTTGCCTGAAGCACTGCAGTGAAGTTGCAGTTGTTCCCATTCGGAACTGGCTCACTAT 2940
 556  L  P  E  A  L  Q  *                                              562

2941 TCCTTTTGCATAATTCGGACTTTTATTTTGGACATTATTGCACTATGCATTTGTTTGTC 3000

3001 ACACCGCGGAACTAAGCCCGAATTC
```

```
5'
       87              96             105             114             123             132
      ATG CTT TCT     AGC ATT ACC     CTC CTA CCT     TTG CTC GCT     GCG GTC TCA     ACC CCC GCC
       M   L   S       S   I   T       L   L   P       L   L   A       A   V   S       T   P   A 141             150             159             168             177             186
      TTT GCT GTC     GCC AAC TAT     CGC TTC GAC     ATC AAG AAC     GTC GCT CCC     ...
       F   A   V       A   N   Y       R   F   D       I   K   N       V   A   P       ...

195             204             213             222             231             240
      GAT GGC TTT     CAG CGC TCT     ATC GTC TCC     GTC AAC GGT     TTA GTT CCT     GGC ACG TTG
       D   G   F       Q   R   S       I   V   S       V   N   G       L   V   P       G   T   L 249             258             267             276             285             294
      ATC ACG GCC     AAC AAG GGT     GAC ACC TTG     CGC ATT AAT     GTC ACG CAA     CTC ACG TTG
       I   T   A       N   K   G       D   T   L       R   I   N       V   T   Q       L   T   L 303             312             321             330             339             348
      AGT ATG CGT     CGT GCC ACA     ACG ATT CAT     TGG CAT GGA     TTG TTC CAA     GCT ...
       S   M   R       R   A   T       T   I   H       W   H   G       L   F   Q       A  ...

GAC CCT ...
       D   P  ...
```

```
     357              366              375              384              393              402
ACT ACC GCC GAC GAG GAT GGC CCC GCA TTC GTC ACG CAA TGC CCT ATT GCG CAA
 T   T   A   D   E   D   G   P   A   F   V   T   Q   C   P   I   A   Q 411              420              429              438              447              456
AAT TTG TCC TAT ACA TAC GAG ATC CCA TTG CGC GGC CAA ACA GGA ACC ATG TGG
 N   L   S   Y   T   Y   E   I   P   L   R   G   Q   T   G   T   M   W 465              474              483              492              501              510
TAT CAC GCC CAT CTT GCG AGT CAA TAT GTC GAT GGA TTG CGA GGC CCT TTG GTC
 Y   H   A   H   L   A   S   Q   Y   V   D   G   L   R   G   P   L   V 519              528              537              546              555              564
ATC TAT GAT CCA AAC GAC CCA CAC AAG TCG CGC TAC GAC GTG GAT GAT GCG AGC
 I   Y   D   P   N   D   P   H   K   S   R   Y   D   V   D   D   A   S 573              582              591              600              609              618
ACA GTA GTC ATG CTT GAG GAC TGG TAC CAT ACT CCG GCA CCC GTT CTA GAA AAG
 T   V   V   M   L   E   D   W   Y   H   T   P   A   P   V   L   E   K
```

```
CAA ATG TTC TCG ACT AAT AAC ACC GCT CTG CTC TCT CCT GTT CCG GAC TCG GGT
 Q   M   F   S   T   N   N   T   A   L   L   S   P   V   P   D   S   G
627         636         645         654         663         672

CTT ATC AAT GGC AAA GGG CGC TAT CGC GTG GGC GGT CCC GCA GTT CCC CGG TCA
 L   I   N   G   K   G   R   Y   R   V   G   G   P   A   V   P   R   S
681         690         699         708         717         726

ATC AAC GTA AAA CGT GGG AAA CGA TAT CGC TTG CGC GTA ATC AAC GCT TCT GCT
 I   N   V   K   R   G   K   R   Y   R   L   R   V   I   N   A   S   A
735         744         753         762         771         780

ATC GGG TCG TTT ACC TTT TCG ATC GAA GGA CAT AGT CTG ACT GTC ATT GAG GCC
 I   G   S   F   T   F   S   I   E   G   H   S   L   T   V   I   E   A
789         798         807         816         825         834

GAT GGG ATC CTG CAC CAG CCC TTG GCT GTT GAC AGC TTC CAG ATT TAC GCT GGA
 D   G   I   L   H   Q   P   L   A   V   D   S   F   Q   I   Y   A   G
843         852         861         870         879         888
```

```
     897           906           915           924           933           942
CAA CGC TAC TCT GTC ATC GTT GAA GCC AAC CAA ACC GCC AAC TAC TGG ATT
 Q   R   Y   S   V   I   V   E   A   N   Q   T   A   N   Y   W   I 951           960           969           978           987           996
CGT GCA CCA ATG ACC GTT GCA GGA GCC GGA ACC AAT GCA AAC TTG GAC CCC ACC
 R   A   P   M   T   V   A   G   A   G   T   N   A   N   L   D   P   T 1005          1014          1023          1032          1041          1050
AAT GTC TTT GCC GTA TTG CAC TAC GAG GGA GCG CCC AAC GCC GAA CCC ACG ACG
 N   V   F   A   V   L   H   Y   E   G   A   P   N   A   E   P   T   T 1059          1068          1077          1086          1095          1104
GAA CAA GGC AGT GCT ATC GGT ACT GCA CTC GTT GAA GAG AAC CTC CAT GCG CTC
 E   Q   G   S   A   I   G   T   A   L   V   E   E   N   L   H   A   L 1113          1122          1131          1140          1149          1158
ATC AAC CCT GGC GCT CCG GGC GGC TCC GCT CCC GCA GAC GTT TCC CTC AAT CTT
 I   N   P   G   A   P   G   G   S   A   P   A   D   V   S   L   N   L
```

FIG. 4D

```
            1167              1176              1185              1194             1203             1212
       GCA ATT GGG CGC AGC ACA GTT GAT GGG ATT CTT AGG TTC ACA TTT AAT AAC ATC
        A   I   G   R   S   T   V   D   G   I   L   R   F   T   F   N   N   I 1221              1230              1239              1248             1257             1266
       AAG TAC GAG GCT CCT TCG TTG CCC ACG CTC TTG AAG ATT TTG GCA AAC AAT GCG
        K   Y   E   A   P   S   L   P   T   L   L   K   I   L   A   N   N   A 1275              1284              1293              1302             1311             1320
       AGC AAT GAC GCC GAT TTC ACG CCA AAT GAG CAC ACT ATC GTA TTG CCA CAC AAT
        S   N   D   A   D   F   T   P   N   E   H   T   I   V   L   P   H   N 1329              1338              1347              1356             1365             1374
       AAA GTT ATC GAG CTC AAT ATC ACC GGA GGT GCA GAC CAC CAT CCT ATC CTC CAC
        K   V   I   E   L   N   I   T   G   G   A   D   H   H   P   I   L   H 1383              1392              1401              1410             1419             1428
       GGC CAT GTG TTT GAT ATC GTC AAA TCA CTC GGT ACC CCG AAC TAT GTC AAC
        G   H   V   F   D   I   V   K   S   L   G   T   P   N   Y   V   N
```

FIG. 4E

```
      1437              1446              1455              1464              1473              1482
CCG CCA CGC AGG GAC GTA GTT CGT GTC GGA GGC ACC GGT GTG GTA CTC CGA TTC
 P   P   R   R   D   V   V   R   V   G   G   T   G   V   V   L   R   F 1491              1500              1509              1518              1527              1536
AAG ACC GAT AAC CCA GGC CCA TGG TTT GTT CAC TGC CAC ATT GAC TGG CAC TTG
 K   T   D   N   P   G   P   W   F   V   H   C   H   I   D   W   H   L 1545              1554              1563              1572              1581              1590
GAG GCT GGG CTC GCA CTT GTC TTT GCC GAG GCC CCC AGC CAG ATT CGC CAG GGT
 E   A   G   L   A   L   V   F   A   E   A   P   S   Q   I   R   Q   G 1599              1608              1617              1626              1635              1644
GTC CAG TCG GTC CAG CCC AAC AAT GCC TGG AAC CAG CTC TGC CCC AAG TAC GCG
 V   Q   S   V   Q   P   N   N   A   W   N   Q   L   C   P   K   Y   A 1653              1662
GCT CTT CCT CCC GAT TTG CAG T 3'
 A   L   P   P   D   L   Q
```

PURIFIED PH NEUTRAL *RHIZOCTONIA LACCASES* AND NUCLEIC ACIDS ENCODING SAME

RELATED APPLICATIONS

This application is a continuation-in-part of U.S. Ser. Nos. 08/122,230 filed Sep. 17, 1993, now abandoned, 08/122,827 filed Sep. 17, 1993, now abandoned, and 08/162,827 filed Dec. 3, 1993, now abandoned, the contents of which are incorporated by reference in their entirety.

FIELD OF THE INVENTION

The present invention relates to isolated nucleic acid fragments encoding a fungal oxidoreductase enzyme and the purified enzymes produced thereby. More particularly, the invention relates to nucleic acid fragments encoding a phenol oxidase, specifically a laccase, which functions at a neutral pH.

BACKGROUND OF THE INVENTION

Laccases (benzenediol:oxygen oxidoreductases) are multi-copper containing enzymes that catalyze the oxidation of phenolics. Laccase-mediated oxidations result in the production of aryloxy-radical intermediates from suitable phenolic substrate; the ultimate coupling of the intermediates so produced provides a combination of dimeric, oligomeric, and polymeric reaction products. Such reactions are important in nature in biosynthetic pathways which lead to the formation of melanin, alkaloids, toxins, lignins, and humic acids. Laccases are produced by a wide variety of fungi, including ascomycetes such as Aspergillus, Neurospora, and Podospora, the deuteromycete Botrytis, and basidiomycetes such as Collybia, Fomes, Lentinus, Pleurotus, Trametes, and perfect forms of Rhizoctoniao. Laccase exhibits a wide range of substrate specificity, and each different fungal laccase usually differs only quantitatively from others in its ability to oxidize phenolic substrates. Because of the substrate diversity, laccases generally have found many potential industrial applications. Among these are lignin modification, paper strengthening, dye transfer inhibition in detergents, phenol polymerization, juice manufacture, phenol resin production, and waste water treatment.

Although the catalytic capabilities are similar, laccases made by different fungal species do have different temperature and pH optima, and these may also differ depending on the specific substrate. A number of these fungal laccases have been isolated, and the genes for several of these have been cloned. For example, Choi et al.(Mol. Plant-Microbe Interactions 5: 119–128, 1992) describe the molecular characterization and cloning of the gene encoding the laccase of the chestnut blight fungus, *Cryphonectria parasitica*. Kojima et al. (J. Biol. Chem. 265: 15224–15230, 1990; JP 2-238885) provide a description of two allelic forms of the laccase of the white-rot basidiomycete *Coriolus hirsutus*. Germann and Lerch (Experientia 41: 801,1985; PNAS USA 83: 8854–8858, 1986) have reported the cloning and partial sequencing of the *Neurospora crassa* laccase gene. Saloheimo et al.(J. Gen. Microbiol. 137: 1537–1544, 1985; WO 92/01046) have disclosed a structural analysis of the laccase gene from the fungus *Phlebia radiata*. However, virtually all of the known fungal laccases function best at acidic pHs (e.g., between pH 3.0 and 6.0), and are typically inactive at neutral or basic pHs. Since a number of the aforestated potential industrial methods are preferentially conducted at neutral or basic pH, most fungal laccases perform poorly in such methods. Thus, the available fungal laccases are inadequate for application in a number of important commercial methods.

An exception to this rule is the extracellular laccase produced by certain species of Rhizoctonia. Bollag et al. have reported a laccase with a pH optimum of about 7.0 produced by *Rhizoctonia praticola*. A laccase of this type would be far more useful in industrial methods requiring neutral pH than previously known laccases. However, the *R. praticola* enzyme was neither purified nor further characterized, nor, to date, has any other laccase having this trait been purified or characterized. Moreover, although other laccase genes have been isolated, as described above, these have been genes encoding enzymes which function best at acidic pH. Recombinant production and commercially adequate yields of a pH neutral or basic laccase have thus been unattainable due to the fact that neither the enzyme per se nor the laccase gene encoding such an enzyme has previously been isolated and/or purified and sequenced. The present invention now provides a solution to each of these problems.

SUMMARY OF THE INVENTION

The present invention relates to an isolated nucleic acid fragment comprising a nucleic acid sequence encoding a Rhizoctonia laccase which functions optimally at a pH between 6.0 to 8.5. By "functioning optimally" is meant that the enzyme exhibits significant(i.e., at least about 30% of maximum, preferably at least about 50%, and most preferably from 50% to maximum) activity within the pH range of between about 6.0–8.5, as determinedly activity in one or more standard laccase assays for substrates such as the syringaldazine, ABTS, 2,6-dimethoxyphenol, or 4 antiaminopyrine+N-ethyl-N-sulfobutyl-m-toluidine. A preferred substrate for the laccases of the present invention is syringaldazine. In a preferred embodiment, the laccase is a *Rhizoctonia solani* laccase. The invention also relates to a substantially pure laccase encoded by the novel nucleic acid sequence. By, "substantially pure" is meant a laccase which is essentially (i.e.,≧90%) free of other non-laccase proteins.

In order to facilitate production of the novel laccase, the invention also provides vectors and host cells comprising the claimed nucleic acid fragment, which vectors and host cells are useful in recombinant production of the laccase. The nucleic acid fragment is operably linked to transcription and translation signals capable of directing expression of the laccase protein in the host cell of choice. A preferred host cell is a fungal cell, most preferably of the genus Aspergillus. Recombinant production of the laccase of the invention is achieved by culturing a host cell transformed or transfected with the nucleic acid fragment of the invention, or progeny thereof, under conditions suitable for expression of the laccase protein, and recovering the laccase protein from the culture.

The laccases of the present invention are useful in a number of industrial processes in which oxidation of phenolics is required. These processes include lignin manipulation, juice manufacture, phenol polymerization and phenol resin production. In a preferred embodiment, the enzyme of the invention is used in a process requiring a neutral or somewhat basic pH for greatest efficiency.

BRIEF DESCRIPTION OF THE FIGURES

FIG. 1 illustrates the nucleotide (SEQ. ID. NO. 1) and amino acid (SEQ. ID. No. 2) sequence of Rslac1. Lower case letters in the nucleotide sequence indicate the position of introns.

FIG. 2 illustrates the nucleotide (SEQ. ID. NO. 3) and amino acid (SEQ. ID. NO. 4) sequence of RSlac2. Lower case letters in the nucleotide sequence indicate the position of introns.

FIG. 4 illustrates the nucleotide (SEQ. ID. NO. 13) and amino acid (SEQ. ID. NO. 14) sequence of the translated region of RSlac3.

DETAILED DESCRIPTION OF THE INVENTION

Figure 3:
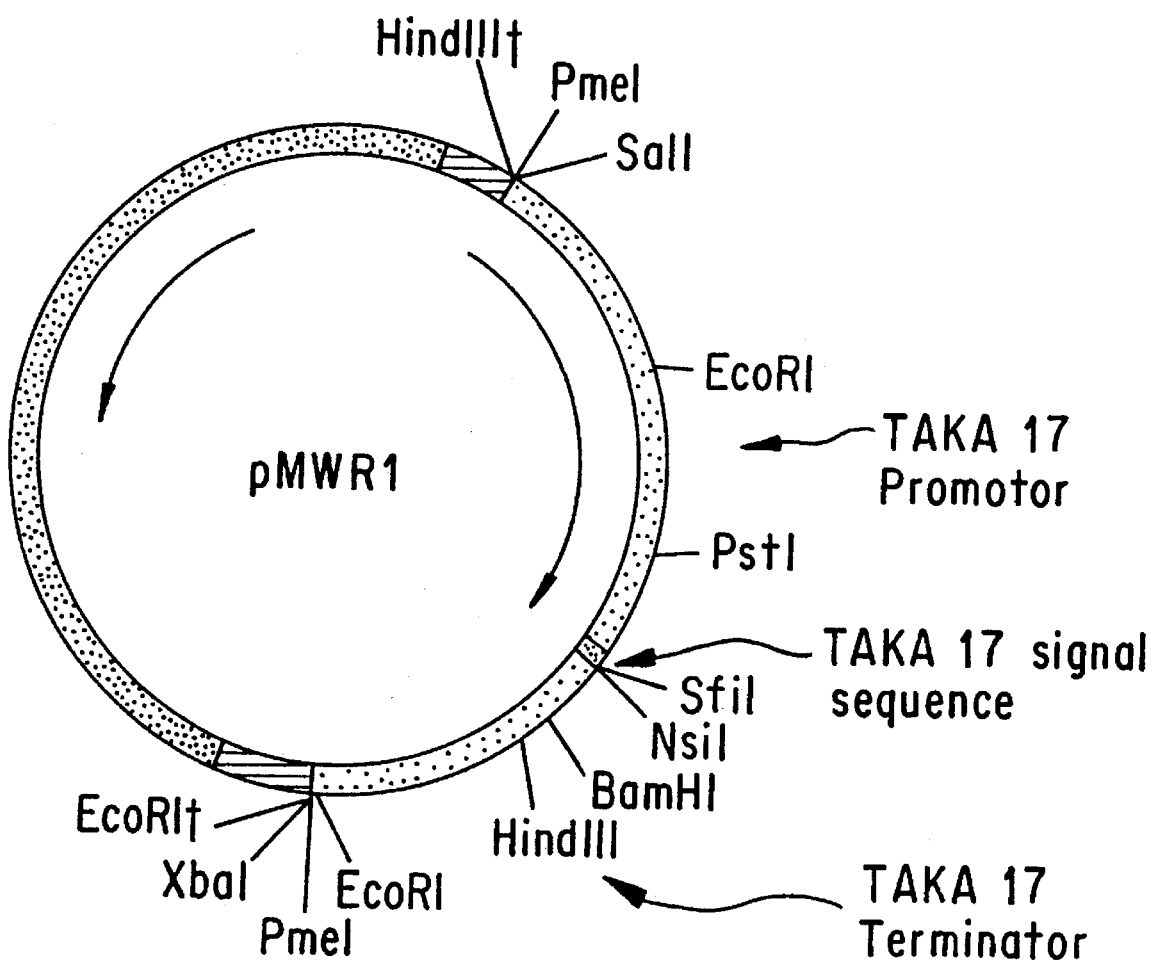
FIG. 3 illustrates a restriction map of the plasmid pMWR-1.

Certain species of the genus Rhizoctonia have been reported as producing laccase; therefore, an initial search focused on identifying the presence of these enzymes in various *Rhizoctonia solani* isolates. Samples are cultured and the supernatants periodically analyzed for the presence of laccase by the ABTS method, described below. Laccase is observed in all the Rhizoctonia cultures. Harvested laccases are electrophoretically separated and stained with ABTS. One isolate, RS22, produces a laccase with a basic pI, and is selected for further study.

The remaining studies focus on purification and characterization of the enzyme from RS22. Briefly, the fermentation broth is filtered and concentrated by UF with a membrane cut off of about 10,000. A first ion exchange chromatography step is conducted at pH 4.5 in acetate buffer, with step elution using NaCl. The eluate is then ultrafiltered and rechromatographed, and eluted with a NaCl gradient. Active fractions are pooled for further study.

The intact protein thus isolated and purified (hereinafter referred to as RSlac3) is first subjected to partial sequencing, and the N-terminal sequence obtained is as follows:

AVRNYKFDIKNVNVAPDGFQRPIVSV (SEQ. ID. NO.: 5)

The protein is further subjected to digestion with a lysine- or glutamic-acid specific protease, and additional peptides obtained from the protein have the following sequences, which can be aligned with sequences in *Coriolus hirsutus*:
Peptide 1:
SQYVDGLRGPLVIYDPDDDH (SEQ. ID. NO: 6)
Peptide 2:
GLALVFAEAPSQIRQGVQSVQPDDA (SEQ. ID. NO.: 7)
Peptide 3:
SRYBVBBASTVVMLEBWYHTPAXVLE (SEQ. ID. NO.: 8)
Peptide 4:
SLGPTPNYVNPXIRDVVRVGGTTVV (SEQ. ID. NO.: 9)
The following peptides are also found, but do not correspond to Coriolus sequences
Peptide 5:
IRYVGGPAVX(N?)RSVI (SEQ. ID. NO.: 10)
Peptide 6:
ILANPA (SEQ. ID. NO.: 11)
Peptide 7:
YEAPSLPT (SEQ. ID. NO.: 12)
In the above sequences, B designates a residue which is either aspartic acid or asparagine, and X designates unidentified residues.

In order to initiate screening for a Rhizoctonia laccase gene, an *R. solani* genomic library is prepared. Total DNA is partially digested with restriction enzyme Sau3A, and electrophoresed in an agarose gel to isolate DNA fragments between 8 and 21 kb in size. The fractionated fragments are ligated to λ phage EMBL3 arms with BamHI ends, and the resulting phage packaged in vitro. These phage are used as a library to create a library of 170,000 plaques in *E. coli* and amplified 100-fold for future use.

In order to develop probes for isolation of the *R. solani* laccase gene, the protein sequences of five known laccases are analyzed to determine consensus sequences, and two degenerate oligonucleotides constructed based on observed consensus sequences (Choi et al. supra; Germann and Lerch, supra; Saloheimo et al, supra, Kojima et al, supra). These oligos are mixed with *R. solani* genomic DNA and a DNA fragment of 220 nucleotide fragment is amplified using a taq polymerase chain reaction(PCR). The 220-nucleotide fragment is then cloned into plasmid vector.

The PCR fragment is used as a probe to screen 25,000 plaques from the amplified genomic library. Positive clones from this screen fall into two classes that are subsequently shown, by DNA sequence analysis, to code for two different laccase genes, RSlac1 and RSlac2. The nucleotide sequence for each of these genes (SEQ ID. NOS.: 1 and 3), and the predicted amino acid sequence for each protein (SEQ. ID. NOS.: 2 and 4), are presented in, respectively, FIGS. 1 and 2. The homology between the two sequences is approximately 63%. Compared to known laccase sequences from *Coriolus hirsutus, Phlebia radiata, Aspergillus nidulans, Crylghonectria parasitica*, and *Neurospora crassa*, the RS laccases show between about 30–40% homology. Each of the two coding sequences is cloned into an expression vector operably linked to *Aspergillus oryzae* taka-amylase transcription and translation signals (See FIG. 3). Each of the two laccase expression vectors is transformed into an *Aspergillus oryzae* and *Aspergillus niger* host cell, and the host cells screened for the presence of laccase.

For isolation of the RSlac3 gene, polyA RNA is purified from *R. solani* mycelia grown in the presence of anisidine. The RNA is used as a template for cDNA synthesis. The cDNA is fractionated and fragments between 1.7–3.5 kb collected, and a cDNA library created by cloning the fractionated DNA into a yeast vector. 3000 transformants from this library are screened on ABTS. After 24 hours, a single colony appears positive. The plasmid from the colony is isolated and the insert sequenced. Portions of the predicted amino acid sequence correspond with the sequences of the fragments obtained from RS 22, described supra. The complete nucleotide and amino acid sequences are depicted in FIG. 4, and in SEQ. ID. NOS.: 13 and 14, respectively. RSlac3 shows 48% homology with Rslac1 and 50% homology with RSlac2. RSlac3 also shows 48% homology with the *Coriolus hirsutus* laccase gene.

According to the invention, a Rhizoctonia gene encoding a pH neutral or basic laccase can be obtained by methods described above, or any alternative methods known in the art, using the information provided herein. The gene can be expressed, in active form, using an expression vector. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene or various activator genes. To permit the secretion of the expressed protein, nucleotides encoding a signal sequence may be inserted prior to the coding sequence of the gene. For expression under the direction of control sequences, a laccase gene to be treated according to the invention is operably linked to the control sequences in the proper reading frame. Promoter sequences that can be incorporated into plasmid vectors, and which can direct the transcription of the laccase gene, include but are not limited to the prokaryotic β-lactamase promoter (Villa-Kamaroff, et al., 1978, Proc. Natl. Acad. Sci. U.S.A. 75:3727–3731) and the tac promoter (DeBoer, et al., 1983, Proc. Natl. Acad. Sci. U.S.A. 80:21–25). Further references can also be found in "Useful proteins from recombinant bacteria" in Scientific American, 1980, 242:74–94; and in Sambrook et al., Molecular Cloning, 1989.

The expression vector carrying the DNA construct of the invention may be any vector which may conveniently be subjected to recombinant DNA procedures, and the choice of vector will typically depend on the host cell into which it is to be introduced. Thus, the vector may be an autonomously replicating vector, i.e. a vector which exists as an extrachromosomal entity, the replication of which is independent of chromosomal replication, e.g. a plasmid, or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA construct of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), or the promoters of the *Bacillus subtilis* xy1A and xy1B genes. In a yeast host, a useful promoter is the eno-1 promoter. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamsii* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters.

The expression vector of the invention may also comprise a suitable transcription terminator and, in eukaryotes, polyadenylation sequences operably connected to the DNA sequence encoding the laccase of the invention. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B.subtilis* or *B.licheniformis*, or one which confers antibiotic resistance such as ampicillin, kanamycin, chloramphenicol or tetracycline resistance. Examples of Aspergillus selection markers include amdS, pyrG, argB, niaD and sC, a marker giving rise to hygromycin resistance. Preferred for use in an Aspergillus host cell are the amdS and pyrG markers of *A. nidulans* or *A. oryzae*. A frequently used mammalian marker is the dihydrofolate reductase (DHFR) gene. Furthermore, selection may be accomplished by co-transformation, e.g. as described in WO 91/17243.

It is generally preferred that the expression is extracellular. The laccases of the present invention may thus comprise a preregion permitting secretion of the expressed protein into the culture medium. If desirable, this preregion may be native to the laccase of the invention or substituted with a different preregion or signal sequence, conveniently accomplished by substitution of the DNA sequences encoding the respective preregions. For example, the preregion may be derived from a glucoamylase or an amylase gene from an Aspergillus species, an amylase gene from a Bacillus species, a lipase or proteinase gene from *Rhizomucor miehei*, the gene for the α-factor from Saccharomyces cerevisiae or the calf prochymosin gene. Particularly preferred, when the host is a fungal cell, is the preregion for *A. oryzae* TAKA amylase, *A. niger* neutral amylase, the maltogenic amylase form Bacillus NCIB 11837, *B. stearothermophilus* α-amylase, or *Bacillus licheniformis* subtilisin. An effective signal sequence is the *A. oryzae* TAKA amylase signal, the *Rhizomucor miehei* aspartic proteinase signal and the *Rhizomucor miehei* lipase signal.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. Molecular Cloning, 1989).

The cell of the invention either comprising a DNA construct or an expression vector of the invention as defined above is advantageously used as a host cell in the recombinant production of a enzyme of the invention. The cell may be transformed with the DNA construct of the invention, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The host cell may be selected from prokaryotic cells, such as bacterial cells. Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus*, or gram negative bacteria such as *E. coli*. The transformation of the bacteria may for instance be effected by protoplast transformation or by using competent cells in a manner known per se.

The host cell may also be a eukaryote, such as mammalian cells, insect cells, plant cells or preferably fungal cells, including yeast and filamentous fungi. For example, useful mammalian cells include CHO or COS cells. A yeast host cell may be selected from a species of Saccharomyces or Schizosaccharomyces, e. g. *Saccharomyces cerevisiae*. Useful filamentous fungi may selected from a species of Aspergillus, e.g. *Aspergillus oryzae* or *Aspergillus niger*. Alternatively, a strain of a Fusarium species, e.g. *F.*

*oxysporum*, can be used as a host cell. Fungal cells may be transformed by a process involving protoplast formation and transformation of the protoplasts followed by regeneration of the cell wall in a manner known per se. A suitable procedure for transformation of Aspergillus host cells is described in EP 238 023. A suitable method of transforming Fusarium species is described by Malardier et al., 1989.

The present invention thus provides a method of producing a recombinant laccase of the invention, which method comprises cultivating a host cell as described above under conditions conducive to the production of the enzyme and recovering the enzyme from the cells and/or culture medium. The medium used to cultivate the cells may be any conventional medium suitable for growing the host cell in question and obtaining expression of the laccase of the invention. Suitable media are available from commercial suppliers or may be prepared according to published formulae (e.g. in catalogues of the American Type Culture Collection).

The resulting enzyme may be recovered from the medium by conventional procedures including separating the cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, gel filtration chromatography, affinity chromatography, or the like. Preferably, the isolated protein is about 90% pure as determined by SDS-PAGE, purity being most important in food, juice or detergent applications.

In a particularly preferred embodiment, the expression of laccase is achieved in a fungal host cell, such as Aspergillus. As described in detail in the following examples, the laccase gene is ligated into a plasmid containing the *Aspergillus oryzae* TAKA α-amylase promoter, and the *Aspergillus nidulans* amdS selectable marker. Alternatively, the amdS may be on a separate plasmid and used in co-transformation. The plasmid (or plasmids) is used to transform an Aspergillus species host cell, such as *A. oryzae* or *A. niger* in accordance with methods described in Yelton et al. (PNAS USA 81: 1470–1474,1984).

Those skilled in the art will recognize that the invention is not limited to use of the nucleic acid fragments specifically disclosed herein, for example, in FIGS. 1 and 2. It will be apparent that the invention also encompasses those nucleotide sequences that encode the same amino acid sequences as depicted in FIGS. 1, 2 and 3, but which differ from those specifically depicted nucleotide sequences by virtue of the degeneracy of the genetic code. In addition, the invention also encompasses other nucleotide fragments, and the proteins encoded thereby, which encode laccase proteins having substantially the same pH optimum as those of *Rhizoctonia solani,* and which show a significant level of homology with the *Rhizoctonia solani* amino acid sequence. For example, the present data show that more than one species of Rhizoctonia produces a laccase with the desired pH profile; it is therefore expected that other Rhizoctonia species also produce similar laccases and therefore, using the technology described herein, can be used as a source for genes within the scope of the claimed invention. As also shown in the present examples, not only is there more than one nucleotide and amino acid sequence that encodes a laccase with the required characteristics, there is also considerable variation tolerated within the sequence while still producing a functional enzyme. Therefore, the invention also encompasses any variant nucleotide sequence, and the protein encoded thereby, which protein retains at least about an 80% homology with one or the other of the amino acid sequences depicted in FIGS. 1, 2 and 3, and retains both the laccase and pH optimum activity of the sequences described herein. In particular, variants which retain a high level(i.e., $\geq$ 80%) of homology at highly conserved regions of the Rhizoctonia laccase are contemplated. Such regions are identified as residues 458–469 in RSLAC1, and 478–489 in RSLAC2; and residues 131–144 in RSLAC1 and 132–145 in RSLAC2.

Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln. It will be apparent to the skilled artisan that such substitutions can be made outside the regions critical to the function of the molecule and still result in an active enzyme. Retention of the desired activity can readily be determined by conducting a standard ABTS oxidation method in 0.1M sodium phosphate at pH 7.0.

The protein can be used in number of different industrial processes; although the enzyme is also functional to some extent at lower pH, the *R. solani* laccase is most beneficially used in processes that are usually conducted at a neutral or alkaline pH, since other laccases are not active in this pH range. These processes include polymerization of lignin, both Kraft and lignosulfates, in solution, in order to produce a lignin with a higher molecular weight. A neutral/alkaline laccase is a particular advantage in that Kraft lignin is more soluble at higher pHs. Such methods are described in, for example, Jin et al., Holzforschung 45(6): 467–468, 1991; U.S. Pat. No. 4,432,921; EP 0 275 544; PCT/DK93/00217, 1992.

The laccase of the present invention can also be used for in-situ depolymerization of lignin in Kraft pulp, thereby producing a pulp with lower lignin content. This use of laccase is an improvement over the current use of chlorine for depolymerization of lignin, which leads to the production of chlorinated aromatic compounds, which are an environmentally undesirable by-product of paper mills. Such uses are described in, for example, Current opinion in Biotechnology 3: 261–266, 1992; J. Biotechnol. 25: 333–339, 1992; Hiroi et al., Svensk papperstidning 5: 162–166, 1976. Since the environment in a paper mill is typically alkaline, the present laccase is more useful for this purpose than other known laccases, which function best under acidic conditions.

Oxidation of dyes and other chromophoric compounds leads to decolorization of the compounds. Laccase can be used for this purpose, which can be particularly advantageous in a situation in which a dye transfer between fabrics is undesirable, e.g., in the textile industry and in the detergent industry. Methods for dye transfer inhibition and dye oxidation can be found in WO 92/01406, WO 92/18683, EP 0495836 and Calvo, Mededelingen van de Faculteit Landbouwwetenschappen/Rijiksuniversitet Gent.56: 1565–1567, 1991.

The present laccase can also be used for the polymerization of phenolic compounds present in liquids. An example of such utility is the treatment of juices, such as apple juice, so that the laccase will accelerate a precipitation of the phenolic compounds present in the juice, thereby producing a more stable juice. Such applications have been described in Stutz, Fruit processing 7/93, 248–252, 1993; Maier et al., Dt. Lebensmittel-rindschau 86(5): 137–142, 1990; Dietrich et al., Fluss. Obst 57(2): 67–73, 1990. The invention is further illustrated by the following non-limiting examples.

EXAMPLES

1. Purification and characterization of R. solani Laccase

Individual isolates of R. solani cultured on potato dextrose agar (Difco) are examined for laccase enzyme formation by transferring a small piece of agar containing vigorous growth to 100 ml CFM (24.0 g potato dextrose broth, 3.0 g yeast extract, 1.0 ml Microelement solution [0.80 g $KH_2PO_4$, 0.64 g $CUSO_4.5H_2O$, 0.11 g $FeSO_4.7H_2O$, 0.80 g $MnCl_2.4H_2O$, 0.15 g $ZnSO_4.7H_2O$, distilled water to 1000 ml], distilled water to 1000 ml) in a 500 ml shake flask. Incubation is at room temperature, at 200 rpm on an orbital shaker.

Samples are harvested at 50, 74, 122 and 170 hours, centrifuged and the clear supernatant analyzed for laccase with its ABTS (ABTS=2,2'-azinobis (3 ethylbenzothiazoline-6-sulfonic acid). The analysis is carried out by adding 200 µl of 2 mM ABTS in 0.1M phosphate buffer, pH 7, and observing the change in absorbance at 418 nm after 30 minutes incubation at room temperature (approximately 23°–25° C.). This method is modified from a peroxidase analysis method described by Pütter and Becker (Peroxidases, in: Bergmeyer, H. U. (ed.), Methods of Enzymatic Analysis, 3rd ed., Vol. III, pp.286–293, 1983)

Each of the laccases harvested at 172 hours is electrophoretically separated and stained with ABTS as chromogen. Several distinct patterns emerge; the strain RS 22 is shown to produce a laccase having a basic pI, and is chosen for further characterization.

Laccase acclivity is also determinable by the syringaldazine method. Laccase catalyzes the oxidation of syringaldazine to tetramethoxy azo bis-methylene quinone under aerobic conditions, with a change of color from yellow to violet. 3000 µl of 25 mM acetate buffer (containing 10 mg/l cuprisulfate, 5 $H_2O$) at pH 5.5, 30° C., is mixed in a 1 cm cuvette with 225 µmM syringaldazine (5 mg solubilized in 25 ml ethanol and adjusted to 50 ml with demineralized water). The mixture is then mixed with 100 µl of a laccase dilution (diluted in acetate buffer so that the increase in absorbance($\Delta$OD) is within the range of 0.1–0.6). The reaction mixture is placed in a 30° C. thermostated spectrophotometer and the reaction is followed at 530 nm for 10 to 70 seconds from the addition of laccase. The activity of the enzyme is calculated as $\Delta$OD/minute×0.677×dilution factor, and is expressed as LACU.

For purification of the Rhizoctonia laccase, 2.1 liter of culture medium with a LACU activity of 0.19 LACU/ml is filtered through a 10 µm filter and concentrated to 230 ml by ultrafiltration using a Filtron Minisette OMEGA membrane with a cutoff value of 10 kDa. The pH of the sample is 5.3 and the activity of the concentrated sample is determined to be 3.34 LACU/ml.

After pH adjustment to 4.5 and filtration due to slight precipitation, the sample is applied to a 40 ml S Sepharose Fast Flow column equilibrated with 20 mM acetate buffer at pH 4.5 (buffer A). The column is washed in buffer A and eluted with buffer A containing 1M NaCl. Active fractions are collected and pooled. This active pool is concentrated and buffer exchanged to buffer A using an Amicon ultrafiltration unit equipped with a Diaflo YM10 membrane. This sample is rechromatographed on a 5 ml S Sepharose High Performance column using the method described above except that elution is carried out with a linear gradient over 30 column volumes from buffer A to buffer A containing 0.5M NaCl. The fractions from this purification exhibiting highest activity are pooled. Approximately 45 mg laccase are obtained, when protein concentration is estimated by one absorption unit at A280 nm equal to 1 mg/ml. The protein is >90% pure as judged by SDS-PAGE. The molecular weight estimated by SDS-PAGE is approximately 67 kDa. The specific activity of the purified protein is 1 LACU/mg. The pH profile of the purified protein, using syringaldazine as substrate is show in Table 1, below.

TABLE 1

| pH | 5 | 6 | 7 | 8 |
|---|---|---|---|---|
| % activity | 0.5 | 31 | 100 | 59 |

For sequencing of the protein, peptides are generated using wither a lysine-specific protease from Achromobacter (Achromobacter protease I) or a glutamic acid specific protease from *Bacillus licheniformes*. The peptides are purified by reverse phase HPLC employing linear gradients of 80% 2-propanol containing 0.08% aqueous TFA (solvent B) in 0.1% aqueous TFA (solvent A).

N-terminal amino acid sequence analysis of the intact protein and of purified peptides are carried out in an Applied Biosystems 473A protein sequencer according to the manufacturer's instructions. Initial partial sequencing of the isolated protein yields the following N-terminal sequence:

AVRNYKFDIKNVNVAPDGFQRPIVSV (SEQ. ID. NO.: 5)

The protein is then digested with either a lysine- or glutamic-acid specific protease, and following additional peptides identified. Peptides 1–4 can be aligned with sequences in the laccase of *Coriolus hirsutus*:

Peptide 1:
SQYVDGLRGPLVIYDPDDDH (SEQ. ID. NO: 6)
Peptide 2:
GLALVFAEAPSQIRQGVQSVQPDDA (SEQ. ID. NO.: 7)
Peptide 3:
SRYBVBBASTVVMLEBWYHTPAXVLE (SEQ. ID. NO. 8)
Peptide 4:
SLGPTPNYVNPXIRDVVRVGGTTVV (SEQ. ID. NO. 9)
Peptide 5:
IRYVGGPAVX (N?)RSVI (SEQ. ID. NO.: 10)
Peptide 6:
ILANPA (SEQ. ID. NO.: 11)
Peptide 7:
YEAPSLPT (SEQ. ID. NO.: 12)

An X in the above sequences designates an unidentified residue, and B represents a residue which is either aspartic acid or asparagine.

2. Isolation of R. solani laccase gene

A study of the known amino acid sequences of fungal laccases obtained from non-Rhizoctonia species (Choi et al., supra; German et al., supra; Saloheimo et al. supra; and Kojima et al, supra) is conducted to determine the presence of consensus sequences among them. Two regions of high identity, IHWHGFFQ and TFWYHSH, are found near the amino terminal third of the protein. Based on these consensus sequences and the corresponding DNA sequences, three degenerate oligonucleotides, O-lac2 [TGG/AAAGAC-CATA/GGTGTCG/AGTA/G], its complement O-lac2r, and O-lac3 [ATCCAT/CTGGCAT/CGGG/CA/TTCTTCCAG/A], are synthesized using an Applied Biosystems 394 DNA/RNA synthesizer.

The synthesized oligos are used in a polymerase chain reaction (PCR) to screen *Rhizoctonia solani* genomic DNA for a laccase gene or fragment thereof. For amplifications of genomic DNA, 0.5 µg of genomic DNA is incubated with 1 µM of each primer, 200 µM of dNTPs, and 1 U taq polymerase (Boehringer Mannheim) in [10 mM Tris-Cl, 1.5 mM $MgCl_2$, 50 mM KCl, 1 mg/ml gelatine;pH 8.3. The reactions are incubated for 1×5 minutes at 95° C., 30×[1 minute at 95° C., 1 minute at 50°–60° C., 1 minute at 72° C.], and 1×5 minutes at 72° C. The PCR reactions amplify a DNA fragment of 220 nucleotides. The PCR product is cloned, according to manufacturer's directions, into the TA cloning vector (InVitrogen Corp.). Characterization of the PCR product by DNA sequencing of individual clones distinguishes two separate laccase genes designated Rslac1 and RSlac2.

To prepare a *R. solani* genomic library, *R. solani* DNA is partially digested with restriction enzyme Sau3A, and electrophoresed through a 0.8% Sea Plaque Agarose (FMC Bioproducts) in a Tris/Acetate/EDTA buffer to isolate those DNA fragments between 8.0 an 21 kb in size. The gel fractionated fragments are further purified with Beta-Agarase (New England Biolabs) according to manufacturer's instruction, and then ligated to lambda phage EMBL3 arms with BamHI ends. The resulting phages are packaged in vitro using Gigapack II packaging extract(Stratagene). 25 ml of TB media+0.2% maltose and 10 $MgSO_4$ is inoculated into a 50 µl aliquot of an overnight culture of *E. coli* K802 (supE, hsdR, gal, metB) and incubated at 37° C. with shaking until the A600=0.5. 25 µl of a 1:10 and 1:50 dilution of the packaged phage are mixed with 250 µl of the K802 cells, and incubated for 20 minutes at 37° C. To each dilution, 5 µl of melted top agar at 48° C. are added. The mix is then plated onto prewarmed LB plates and incubated at 37° C. for at least 12 hours. From these phage, a library of 170,000 plaques in *E. coli* K802 is created and amplified 100-fold for future use.

To screen for the laccase gene, 25,000 plaques from the amplified genomic library are plated onto NZY/agarose plates for plaque lifts using conventional methods. Filters are screened using the 220 nucleotide PCR fragment randomly labelled to $5 \times 10^8$ cpm/µg as a probe. Filters are hybridized in 50% formamide, 6×SSC for 16 hours at 42° C. and washed with 0.5×SSC, 0.1% SDS at 65° C. Positive clones are picked and rescreened using conventional methods. The nine positive clones identified fell into two classes that by DNA sequence analysis are shown to code for two different laccase genes, Rslac1 and RSlac2. The complete nucleotide sequence of each of these genes is determined using fluorescent nucleotides and an Applied Biosystems automatic DNA sequencer (Model 363A, version 1.2.0). The nucleotide and predicted amino acid sequences are depicted in FIGS. 1 and 2.

For isolation of RSlac3, poly A RNA purified from *R. solani* mycelia grown in the presence of 1 mM anisidine is used as a template for cDNA synthesis using standard protocols. The cDNA is fractionated by electrophoresis through a 0.8% agarose gel and DNA fragments between 1.7 and 3.5 kb in size are collected. A library is then created by cloning the size-fractionated cDNA into the yeast expression vector pYES2. 3000 yeast transformants from this library are plated initially on YNB (1.7 g yeast nitrogen base without amino acids, 5 g $(NH_4)_2SO_4$ per liter) with 2% glucose. After 4 days growth at 30° C., the resulting colonies are replica plated to YNB with 0.1% glucose, 2% galactose and 2 mM ABTS [2,2'-azino-bis(3-ethylbenzthiazoline-6-sulfonic acid; Sigma #A-1888). After 24 hours of growth at 30° C. a single colony has a light green halo which gradually turns a dark purple. The plasmid from this colony is isolated and the insert sequenced. The sequence of the translated portion of the RSlac3 gene and protein is shown in SEQ. ID NOS. 13 and 14, and in FIG. 4.

3. Expression of laccase gene

The plasmid pMWR-1 is a pUC derived vector containing the TAKA amylase transcription regulation signals and the TAKA amylase signal sequence. This plasmid is engineered with a unique SfiI site at the signal sequence cleavage site, and a 3' adjacent NsiI site such that these two restriction enzymes can be used to introduce, in frame, a foreign protein. Using a PCR reaction (conducted as described above, but with 100 ng of the appropriate linearized plasmid DNA as a template) and mutagenized primers, an SfiI site is introduced at amino acid 12 and amino acid 14 of Rslac1 and RSlac2, respectively, such that the protein coding sequences are in frame with the TAKA signal sequence. In addition, a PCR amplification is also used to introduce a PstI site (CTGCAG) at the 3' end of Rslac1 and an NsiI site (ATGCAT) at the 3' end of RSlac2.

To prepare for transformation, cells of *Aspergillus oryzae* are cultivated in YPG (1 g/l yeast extract, 0.25 g $K_2PO_4$. 0.125 g/$MgSO_4$, 3.75 g glucose) at 34° C. with 100–120 rpm for 16–20 hours, then collected by filtration with miracloth. Cells are washed with Mg solution (0.6M $MgSO_4.7H_2O$), then 2–6 g of cells are taken up in 10 ml MgP(1.2M $MgSO_4.7H_2O$, 10 mM $NaH_2PO_4.2H_2O$;pH 5.8). To this is added 1 ml of Novozyme® 234 (120 mg/ml MgP), and the sample kept on ice for 5 minutes. One ml of BSA (12 mg/ml) is added, and the sample shaken gently at 34°–37° C. Protoplasts are collected by filtration through miracloth, and overlain with 5 ml of ST (0.6M Sorbitol, 100 mM Tris; pH 7). The sample is spun at 2500 rpm for 15 minutes, and a band of protoplasts collected. Two volumes of STC (1.2M Sorbitol, 10 mM tris, 10 mM $CaCl_2.2H_2O$;pH 7.5) are added and the sample is spun at 2500 rpm for 5 minutes. The precipitate is washed twice with 5 ml of STC, and the protoplasts suspended in 0.5–1 ml of STC.

For the transformation process, the protoplast concentration is adjusted to $1–5 \times 10^7$/ml. To 100 µl of protoplast solution is added a maximum of 10 µl of DNA solution (5–10 µg of supercoiled DNA) and 0.2 ml of PEG (60% PEG4000, 10 mM Tris, 10 mM $CaCl_2.H_2O$; ph 7.5), and the combination is mixed well. The sample is kept at room temperature for 25 minutes; then to it is added first 0.2 ml PEG, with mixing, the 0.85 ml PEG with mixing. The mixture is kept at room temperature for 20 minutes, then spun at 4000 rpm for 15 minutes. The precipitate is washed with 2 ml of STC by spinning at 2500 rpm for 10 minutes. The protoplasts are resuspended in 0.2–0.5 ml of STC, and then spread on COVE plates. COVE medium (pH 7) contains 342.3 g/l sucrose, 25 g/l agar and a salt solution comprising 26 g/l KCl, 26 g/l $MgSO_4.H_2O$, 76 g/l $KH_2PO_4$, and 50 ml/l of trace metals; the trace metals are 40 mg/l $NaB_4O_7.10H_2O$, 400 mg/l $CuSO_4.5H_2O$, 1200 mg/l $FeSO_4.7H_2O$, 700 mg/l $MnSO_4.H_2O$, 800 mg/l $Na_2MoO_2.2H_2O$, 10 g/l $ZnSO_4.7H_2O$). After autoclaving, 10 ml/l of 1M filtrated acetamide and 5–10 ml of 3M CsCl are added to the solution. Transformants are selected by growth cells on COVE medium which contains acetamide as the carbon source.

The confirmation of laccase production in the samples is determined by the ABTS oxidation method as described above on Cove medium with 2 mM ABTS, at pH 5 and 7.3. Both Rslac1 and RSlac2 express laccase activity at pH 5 and pH 7, in contrast with a control laccase which shows substantially no activity at pH 7.3.

Figure 5:
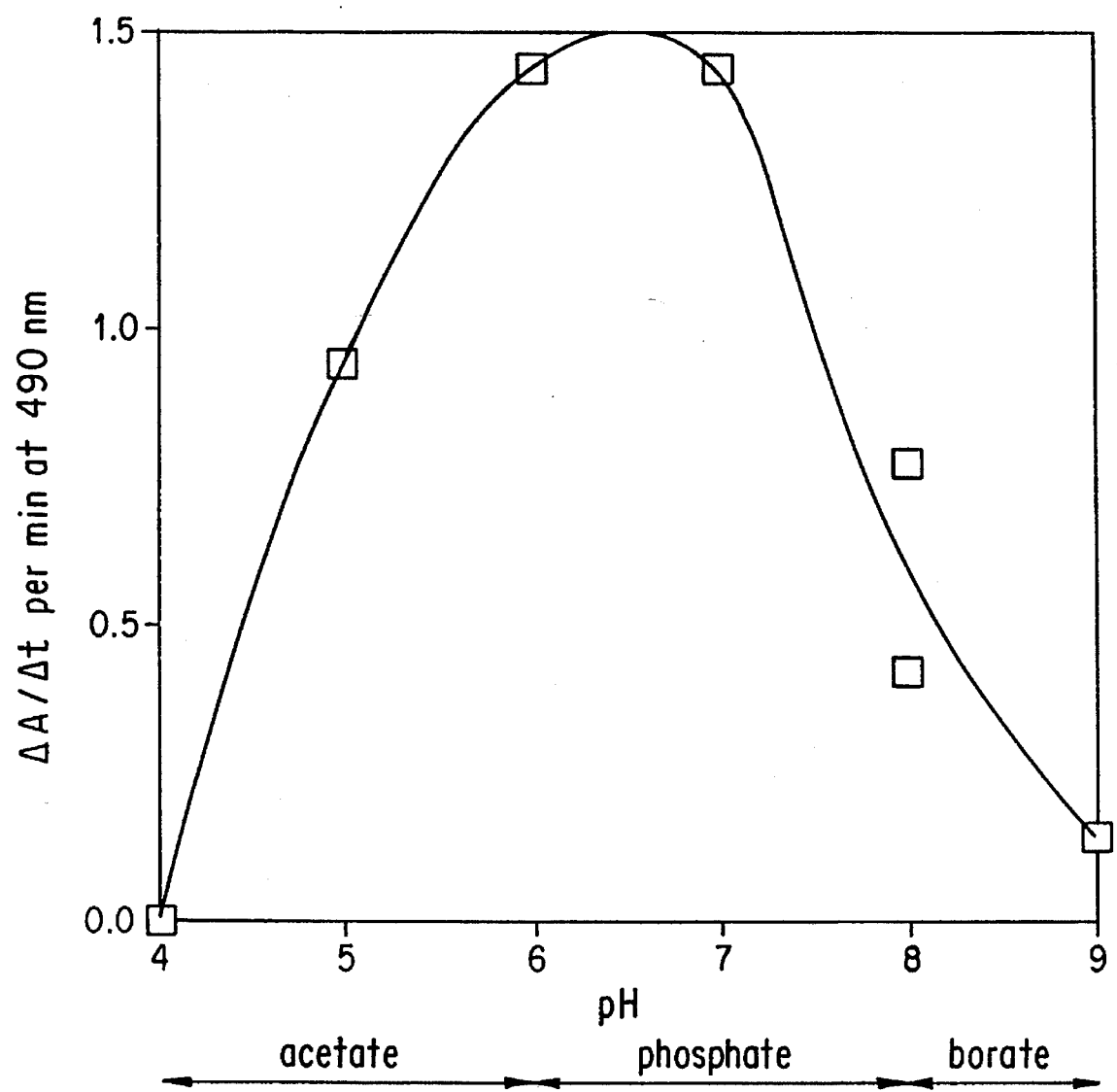
FIG. 5 illustrates the syringaldazine oxidase activity of Rslac1 (90 mM buffer, 20 µM syringaldazine, 20° C.).
Figure 6:
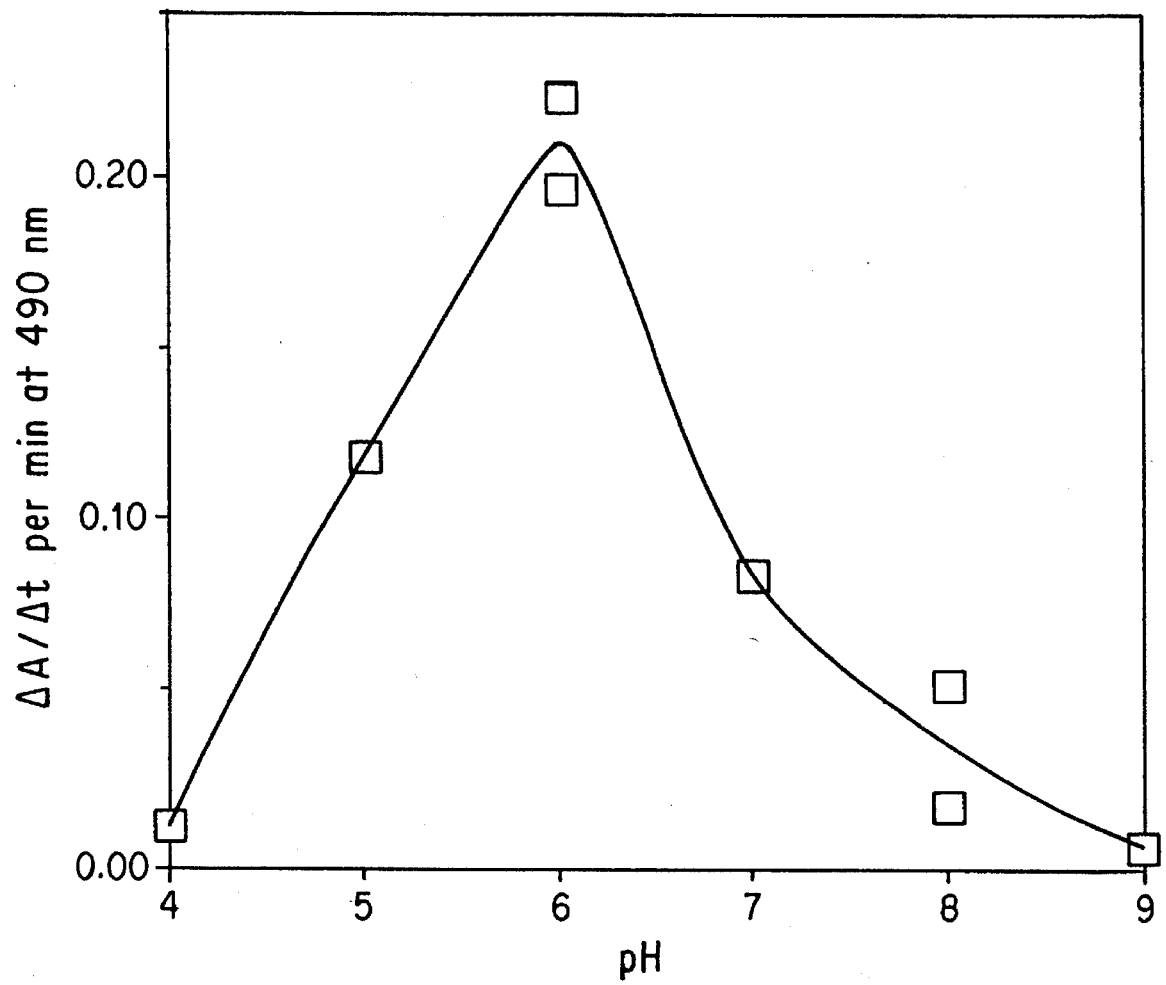
FIG. 6 illustrates the syringaldazine oxidase activity of RSlac2 (93 mM buffer, 20 µM syringaldazine, 20° C.).

The products of the expression of each of Rslac1 and RSlac2 are tested for oxidase activity at various pHs using syringaldazine as the substrate. The assay is conducted substantially as described above for the assay of the native protein, over pH range of 4–9. As shown in FIGS. 5 and 6, both laccases are active at pHs over pH 5, and Rslac1 has particularly good activity at pHs over 6. The pattern of activity is generally comparable to that observed for the RSlac3 laccase isolated from RS 22 (see Table 1 above), with Rslac1 exhibiting the broadest range of activity.

Deposit of Biological Materials

The following biological materials have been deposited under the terms of the Budapest Treaty in the International Mycological Institute, Genetic Resource Reference Collection, located at Bakeham Lane, Egham, Surrey TW20 9TY and given the following accession number.

| Deposit | Accession Number |
| --- | --- |
| *Rhizoctonia solani* RS22 | IMI CC 358730 |

The following biological materials have been deposited under the terms of the Budapest Treaty with the Agricultural Research Service Patent Culture Collection, Northern Regional Research Center, 1815 University Street, Peoria, Ill., 61604 and given the following accession numbers.

| Deposit | Accession Number |
| --- | --- |
| *E. coli* containing RSlac1 fused to an α-amylase signal sequence (EMCC 00844) | NRRL B-21141 |
| *E. coli* containing RSlac2 with an SfiI site insert (EMCC 00845) | NRRL B-21142 |
| *E. coli* containing RSlac3 (EMCC 0088) | NRRL B-21156 |

What we claim is:

1. An isolated nucleic acid fragment containing a nucleic acid sequence encoding a *Rhizoctonia solani* laccase which functions optimally at a pH between about 6.0 and 8.5.

2. The fragment of claim 1 which comprises a nucleic acid sequence encoding the amino acid sequence depicted in SEQ ID NO. 2.

3. The fragment of claim 1 which comprises a nucleic acid sequence encoding the amino acid sequence depicted in SEQ ID NO. 4.

4. The fragment of claim 1, which comprises a nucleic acid sequence encoding a protein containing one or more of the amino acid sequences depicted in SEQ. ID NOS. 5, 6, 7, 8, 9, 10, 11, or 12.

5. The fragment of claim 1 which comprises a nucleic acid sequence encoding the amino acid sequence depicted in SEQ ID NO. 14.

6. The fragment of claim 1, which comprises the nucleic acid sequence depicted in SEQ ID NO. 1).

7. The fragment of claim 1, which comprises the nucleic acid sequence depicted in SEQ. ID. NO. 3.

8. The fragment of claim 1, which comprises the nucleic acid sequence depicted in SEQ. ID. NO. 13.

9. The fragment of claim 1, which comprises the nucleic acid sequence contained in NRRL B-21141.

10. The fragment of claim 1, which comprises the nucleic acid sequence contained in NRRL B-21142.

11. The fragment of claim 1, which comprises the nucleic acid sequence encoding the laccase produced by RS 22.

12. The fragment of claim 1, which comprises the nucleic acid sequence contained in NRRL B-21156.

13. A recombinant vector comprising a nucleic acid fragment of claim 1.

14. The vector of claim 13 in which the fragment is operably linked to a promoter sequence.

15. The vector of claim 14 in which the promoter is a fungal or yeast promoter.

16. The vector of claim 15 in which the promoter is the TAKA amylase promoter of *Aspergillus oryzae*.

17. The vector of claim 15 in which the promoter is the glucoamylase (gluA) promoter of *Aspergillus niger* or *Aspergillus awamsii*.

18. The vector of claim 14 which also comprises a selectable marker.

19. The vector of claim 18 in which the selectable marker is the amdS marker of *Aspergillus nidulans* or *Aspergillus oryzae*.

20. The vector of claim 18 in which the selectable marker is the pyrG marker cf *Aspergillus nidulans, Aspergillus niger, Aspergillus awamsii,* or *Aspergillus oryzae*.

21. The vector of claim 14 which comprises both the TAKA amylase promoter of *Aspergillus oryzae* and the amdS or pyrG marker of *Aspergillus nidulans* or *Aspergillus oryzae*.

22. A host cell comprising a heterologous nucleic acid fragment of claim 1,

23. The host cell of claim 22 which is a fungal cell.

24. The host cell of claim 23 which is an Aspergillus cell.

25. The host cell of claim 22 in which the fragment is integrated into the host cell genome.

26. The host cell of claim 22 in which the fragment is contained on a vector.

27. The host cell of claim 22 which comprises a fragment containing a sequence encoding the amino acid sequence depicted in SEQ ID NO. 2.

28. The host cell of claim 22 which comprises a fragment containing a sequence encoding the amino acid sequence depicted in SEQ ID NO: 4.

29. The host cell of claim 22 which comprises a fragment containing a sequence encoding the amino acid sequence depicted in SEQ ID NO: 14.

30. The host cell of claim 22 which comprises a fragment containing a sequence encoding one or more of the amino acid sequences depicted in SEQ ID NOS.: 5, 6, 7, 8, 9, 10, 11, or 12.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
      ( A ) LENGTH: 2838 base pairs
      ( B ) TYPE: nucleic acid
      ( C ) STRANDEDNESS: single
      ( D ) TOPOLOGY: linear ( i i ) MOLECULE TYPE: DNA (genomic)

( v i ) ORIGINAL SOURCE:
      ( A ) ORGANISM: Rhizoctonia laccase ( i x ) FEATURE:
      ( A ) NAME/KEY: intron
      ( B ) LOCATION: 302..351

( i x ) FEATURE:
      ( A ) NAME/KEY: intron
      ( B ) LOCATION: 463..512

( i x ) FEATURE:
      ( A ) NAME/KEY: intron
      ( B ) LOCATION: 576..633

( i x ) FEATURE:
      ( A ) NAME/KEY: intron
      ( B ) LOCATION: 760..818

( i x ) FEATURE:
      ( A ) NAME/KEY: intron
      ( B ) LOCATION: 822..877

( i x ) FEATURE:
      ( A ) NAME/KEY: intron
      ( B ) LOCATION: 1001..1054

( i x ) FEATURE:
      ( A ) NAME/KEY: intron
      ( B ) LOCATION: 1316..1372

( i x ) FEATURE:
      ( A ) NAME/KEY: intron
      ( B ) LOCATION: 1697..1754

( i x ) FEATURE:
      ( A ) NAME/KEY: intron
      ( B ) LOCATION: 1827..1880

-continued ( i x ) FEATURE:
    ( A ) NAME/KEY: intron
    ( B ) LOCATION: 1992..2051

( i x ) FEATURE:
    ( A ) NAME/KEY: intron
    ( B ) LOCATION: 2157..2206

( i x ) FEATURE:
    ( A ) NAME/KEY: intron
    ( B ) LOCATION: 2348..2404

( i x ) FEATURE:
    ( A ) NAME/KEY: intron
    ( B ) LOCATION: 2438..2498

( i x ) FEATURE:
    ( A ) NAME/KEY: CDS
    ( B ) LOCATION: join(170..301, 352..462, 513..575, 634..759, 819
        . . 821, 878..1000, 1055..1315, 1373..1696, 1755
        . . 1826, 1881..1991, 2052..2156, 2207..2347, 2405
        . . 2437, 2499..2621)

( x i ) SEQUENCE DESCRIPTION: SEQ ID NO:1:

```
AGCGTCACAC CAGACATCGG ATGAAAACGG AAAGTGTATG CGCCATTTGA CGTCTGCGGC       60

AACCACTGTT CATCTCGCGA GCTAACATGG GCGACGTATA AGAAGAACGC GAGAATGGGC      120

AGATTTCGAT ATCCCCTCTC GTCTCGGTTT TGGTCTCGGC TTGCCTCTA ATG GCG         175
                                                      Met Ala
                                                       1

CGC ACC ACT TTC CTT GTC TCG GTT TCG CTC TTT GTT TCC GCT GTT CTT        223
Arg Thr Thr Phe Leu Val Ser Val Ser Leu Phe Val Ser Ala Val Leu
          5              10                  15

GCG CGC ACC GTC GAG TAC GGC TTG AAG ATT AGT GAT GGG GAG ATA GCT        271
Ala Arg Thr Val Glu Tyr Gly Leu Lys Ile Ser Asp Gly Glu Ile Ala
     20                  25                  30

CCT GAC GGT GTT AAG CGT AAT GCG ACT TTG GTACGCACTC CTTGTAATCC          321
Pro Asp Gly Val Lys Arg Asn Ala Thr Leu
 35                  40

AACAATTCAA GGTTTCTGAT GCTTGGTCAG GTA AAT GGA GGG TAT CCC GGT CCA       375
                                 Val Asn Gly Gly Tyr Pro Gly Pro
                                      45                  50

CTC ATT TTT GCC AAC AAG GGG GAT ACT CTC AAA GTC AAG GTC CAA AAC        423
Leu Ile Phe Ala Asn Lys Gly Asp Thr Leu Lys Val Lys Val Gln Asn
             55                  60                  65

AAG CTC ACG AAT CCT GAG ATG TAT CGC ACC ACT TCC ATC GTATGTTCGT         472
Lys Leu Thr Asn Pro Glu Met Tyr Arg Thr Thr Ser Ile
 70                  75                  80

TCGATATCTA CTAATACATC CGTCGCTAAA TATCTTGTAG CAT TGG CAC GGT CTC        527
                                             His Trp His Gly Leu
                                                           85

TTA CAA CAT AGA AAC GCC GAC GAC GAC GGT CCT TCG TTC GTC ACT CAG        575
Leu Gln His Arg Asn Ala Asp Asp Asp Gly Pro Ser Phe Val Thr Gln
             90                  95                 100

GTAGGATTCT GGAAGGTTGG CCTGAACTCT CTGTTAACCG ACAACCCGAT GTCACCAG        633

TGC CCG ATT GTT CCA CGC GAG TCG TAT ACT TAC ACC ATA CCT CTG GAC        681
Cys Pro Ile Val Pro Arg Glu Ser Tyr Thr Tyr Thr Ile Pro Leu Asp
            105                 110                 115

GAT CAA ACC GGA ACC TAT TGG TAC CAT AGC CAC TTG AGT TCG CAA TAC        729
Asp Gln Thr Gly Thr Tyr Trp Tyr His Ser His Leu Ser Ser Gln Tyr
        120                 125                 130

GTT GAT GGT CTT CGA GGC CCG CTG GTA ATC GTGAGTATCT TGACTTGTCT          779
Val Asp Gly Leu Arg Gly Pro Leu Val Ile
135                 140
```

```
ACTGAAGGCA ACGAGACTAA AACAAGCGTC GATTCACAG TAT GTTCGTCTCC              831
                                            Tyr
                                            145

CCTTTATTTA GCTCTGGATC TTCATTTCTC ACGTAATACA TGATAG GAT CCC AAG         886
                                                   Asp Pro Lys

GAT CCT CAC AGG CGT TTG TAT GAT GTT GAC GAT GAG AAG ACC GTC CTG        934
Asp Pro His Arg Arg Leu Tyr Asp Val Asp Asp Glu Lys Thr Val Leu
    150             155             160

ATC ATC GGT GAC TGG TAT CAT GAA TCG TCC AAG GCA ATC CTT GCT TCT        982
Ile Ile Gly Asp Trp Tyr His Glu Ser Ser Lys Ala Ile Leu Ala Ser
165             170             175                 180

GGT AAC ATT ACC CGA CAG GTAAGTGATA CATGCCGGTC CCAGAAAAAT              1030
Gly Asn Ile Thr Arg Gln
                185

TCTCTAAATT CATTTTAATT ACAG CGA CCG GTC TCT GCC ACC ATC AAC GGC        1081
                          Arg Pro Val Ser Ala Thr Ile Asn Gly
                                  190                 195

AAA GGT CGA TTT GAC CCT GAC AAC ACT CCT GCC AAC CCA GAT ACT CTG       1129
Lys Gly Arg Phe Asp Pro Asp Asn Thr Pro Ala Asn Pro Asp Thr Leu
                200             205             210

TAC ACC CTC AAG GTC AAG CGA GGG AAG CGC TAT CGT CTG CGT GTC ATC       1177
Tyr Thr Leu Lys Val Lys Arg Gly Lys Arg Tyr Arg Leu Arg Val Ile
                215             220             225

AAT AGC TCG GAG ATC GCT TCG TTC CGA TTC AGT GTG GAA GGT CAC AAG       1225
Asn Ser Ser Glu Ile Ala Ser Phe Arg Phe Ser Val Glu Gly His Lys
        230             235             240

GTG ACT GTG ATT GCT GCC GAT GGC GTC TCT ACC AAA CCG TAT CAG GTC       1273
Val Thr Val Ile Ala Ala Asp Gly Val Ser Thr Lys Pro Tyr Gln Val
245             250             255

GAT GCG TTT GAT ATT CTA GCA GGA CAG CGC ATA GAT TGC GTC               1315
Asp Ala Phe Asp Ile Leu Ala Gly Gln Arg Ile Asp Cys Val
260             265             270

GTAAGTGTCG TCCGAACCCA CATCTGAGCT CAAGTGTTGA TACATGCGCG CTTATAG        1372

GTG GAG GCG AAC CAA GAA CCC GAC ACA TAC TGG ATC AAC GCA CCG CTG       1420
Val Glu Ala Asn Gln Glu Pro Asp Thr Tyr Trp Ile Asn Ala Pro Leu
275             280             285

ACC AAC GTG CCC AAC AAG ACC GCT CAG GCT CTC CTC GTT TAT GAG GAG       1468
Thr Asn Val Pro Asn Lys Thr Ala Gln Ala Leu Leu Val Tyr Glu Glu
290             295             300             305

GAT CGT CGG CCG TAC CAC CCT CCA AAG GGC CCG TAT CGC AAG TGG AGC       1516
Asp Arg Arg Pro Tyr His Pro Pro Lys Gly Pro Tyr Arg Lys Trp Ser
                310             315             320

GTC TCT GAG GCG ATC ATC AAG TAC TGG AAT CAC AAG CAC AAG CAC GGA       1564
Val Ser Glu Ala Ile Ile Lys Tyr Trp Asn His Lys His Lys His Gly
            325             330             335

CGT GGT TTG CTG TCT GGA CAT GGA GGT CTC AAG GCT CGG ATG ATC GAG       1612
Arg Gly Leu Leu Ser Gly His Gly Gly Leu Lys Ala Arg Met Ile Glu
            340             345             350

GGT AGC CAT CAT CTG CAT TCG CGC AGC GTC GTT AAG CGC CAG AAT GAG       1660
Gly Ser His His Leu His Ser Arg Ser Val Val Lys Arg Gln Asn Glu
            355             360             365

ACC ACC ACT GTT GTA ATG GAC GAG AGC AAG CTC GTT GTAAGTACCA            1706
Thr Thr Thr Val Val Met Asp Glu Ser Lys Leu Val
370                 375             380

TATTTAAAAG TTGGTTGGGT TTCGAATACT TATTTCAACT TTTCTTAG CCA CTG GAA      1763
                                                    Pro Leu Glu

TAC CCC GGC GCT GCA TGC GGG TCT AAA CCT GCT GAC CTC GTC TTG GAT      1811
Tyr Pro Gly Ala Ala Cys Gly Ser Lys Pro Ala Asp Leu Val Leu Asp
385             390             395             400
```

```
CTC ACT TTT GGT TTG GTATGTAGCC AAATCGCCCA TATACAGGAT ACTGAATATT          1866
Leu Thr Phe Gly Leu
            405

GTTTGTGCGT GTAG AAC TTT GCT ACC GGG CAC TGG ATG ATC AAC GGT ATC          1916
                Asn Phe Ala Thr Gly His Trp Met Ile Asn Gly Ile
                                410                 415

CCA TAC GAG TCT CCC AAA ATC CCC ACA TTG CTC AAG ATC CTC ACT GAT          1964
Pro Tyr Glu Ser Pro Lys Ile Pro Thr Leu Leu Lys Ile Leu Thr Asp
        420             425                 430

GAG GAC GGG GTT ACC GAG TCT GAC TTC GTATGTTCCC TTTTCGGTAT               2011
Glu Asp Gly Val Thr Glu Ser Asp Phe
        435             440

CTTCGTATGC GTGCACTGAC TCGTGCTGGT GGGAATTTAG ACC AAG GAG GAG CAC          2066
                                            Thr Lys Glu Glu His
                                                            445

ACA GTC ATA CTC CCG AAG AAC AAA TGC ATC GAA TTC AAC ATC AAG GGG          2114
Thr Val Ile Leu Pro Lys Asn Lys Cys Ile Glu Phe Asn Ile Lys Gly
            450                 455                 460

AAC TCG GGT ATT CCC ATT ACG CAC CCC GTA CAT CTT CAC GGT                  2156
Asn Ser Gly Ile Pro Ile Thr His Pro Val His Leu His Gly
        465             470                 475

GTAAGTGCAT ATCGGATGGT TTACGATACT AAGGCTCATC AACTTTTTAG CAC ACT          2212
                                                        His Thr

TGG GAT GTC GTA CAA TTT GGC AAC AAC CCA CCC AAT TAT GTC AAT CCT          2260
Trp Asp Val Val Gln Phe Gly Asn Asn Pro Pro Asn Tyr Val Asn Pro
480                 485                 490                 495

CCC CGT AGG GAC GTG GTT GGC TCT ACA GAT GCG GGT GTG AGG ATT CAG          2308
Pro Arg Arg Asp Val Val Gly Ser Thr Asp Ala Gly Val Arg Ile Gln
                500                 505                 510

TTC AAG ACC GAC AAT CCA GGA CCG TGG TTC CTG CAC TGC GTGCGTCGGT          2357
Phe Lys Thr Asp Asn Pro Gly Pro Trp Phe Leu His Cys
                515                 520

CCCCATCGTC CGTTATGGTT TTTCTAATAC GTCCCATTCT ATTTTAG CAT ATT GAC          2413
                                                    His Ile Asp
                                                        525

TGG CAT CTT GAG GAG GGT TTC GCA GTGAGTACTG AGACCTAAGT GCTACTCGGC         2467
Trp His Leu Glu Glu Gly Phe Ala
            530                 535

TCATTACTGA TTACCGCATG TATGCGTCTA G ATG GTG TTT GCT GAA GCG CCC          2519
                                  Met Val Phe Ala Glu Ala Pro
                                                          540

GAA GCC GTC AAG GGA GGT CCA AAG AGC GTG GCC GTG GAC TCT CAG TGG          2567
Glu Ala Val Lys Gly Gly Pro Lys Ser Val Ala Val Asp Ser Gln Trp
            545                 550                 555

GAA GGG CTG TGT GGC AAG TAC GAC AAC TGG CTA AAA TCA AAT CCG GGC          2615
Glu Gly Leu Cys Gly Lys Tyr Asp Asn Trp Leu Lys Ser Asn Pro Gly
        560                 565                 570

CAG CTG TAGGCGTATC GCAGCCACAT TGGTGATGAT TGAAAGTTGC ATCTTGTTCC          2671
Gln Leu
575

TATAACCGGC TCTTATATAC GGGTGTCTCC CAGTAAAGTC GTAGCCCAAT TTCAGCCGAG        2731

ACAGATATTT AGTGGACTCT TACTCTTGTG TCCCATTGAC GCACATCGTT GCATCAAACC       2791

TGCTTTTTAT CGTCCCTCTT TGTAATTTGT GTTGCTGTAA TGTATCG                     2838
```

( 2 ) INFORMATION FOR SEQ ID NO:2:

( i ) SEQUENCE CHARACTERISTICS:
        ( A ) LENGTH: 576 amino acids (B) TYPE: amino acid
(D) TOPOLOGY: linear (ii) MOLECULE TYPE: protein (xi) SEQUENCE DESCRIPTION: SEQ ID NO:2:

```
Met Ala Arg Thr Thr Phe Leu Val Ser Val Ser Leu Phe Val Ser Ala
 1               5                  10                  15
Val Leu Ala Arg Thr Val Glu Tyr Gly Leu Lys Ile Ser Asp Gly Glu
                20                  25                  30
Ile Ala Pro Asp Gly Val Lys Arg Asn Ala Thr Leu Val Asn Gly Gly
                35                  40                  45
Tyr Pro Gly Pro Leu Ile Phe Ala Asn Lys Gly Asp Thr Leu Lys Val
        50                  55                  60
Lys Val Gln Asn Lys Leu Thr Asn Pro Glu Met Tyr Arg Thr Thr Ser
 65                  70                  75                  80
Ile His Trp His Gly Leu Leu Gln His Arg Asn Ala Asp Asp Asp Gly
                85                  90                  95
Pro Ser Phe Val Thr Gln Cys Pro Ile Val Pro Arg Glu Ser Tyr Thr
                100                 105                 110
Tyr Thr Ile Pro Leu Asp Asp Gln Thr Gly Thr Tyr Trp Tyr His Ser
            115                 120                 125
His Leu Ser Ser Gln Tyr Val Asp Gly Leu Arg Gly Pro Leu Val Ile
    130                 135                 140
Tyr Asp Pro Lys Asp Pro His Arg Arg Leu Tyr Asp Val Asp Asp Glu
145                 150                 155                 160
Lys Thr Val Leu Ile Ile Gly Asp Trp Tyr His Glu Ser Ser Lys Ala
                165                 170                 175
Ile Leu Ala Ser Gly Asn Ile Thr Arg Gln Arg Pro Val Ser Ala Thr
                180                 185                 190
Ile Asn Gly Lys Gly Arg Phe Asp Pro Asp Asn Thr Pro Ala Asn Pro
                195                 200                 205
Asp Thr Leu Tyr Thr Leu Lys Val Lys Arg Gly Lys Arg Tyr Arg Leu
        210                 215                 220
Arg Val Ile Asn Ser Ser Glu Ile Ala Ser Phe Arg Phe Ser Val Glu
225                 230                 235                 240
Gly His Lys Val Thr Val Ile Ala Ala Asp Gly Val Ser Thr Lys Pro
                245                 250                 255
Tyr Gln Val Asp Ala Phe Asp Ile Leu Ala Gly Gln Arg Ile Asp Cys
                260                 265                 270
Val Val Glu Ala Asn Gln Glu Pro Asp Thr Tyr Trp Ile Asn Ala Pro
            275                 280                 285
Leu Thr Asn Val Pro Asn Lys Thr Ala Gln Ala Leu Leu Val Tyr Glu
    290                 295                 300
Glu Asp Arg Arg Pro Tyr His Pro Pro Lys Gly Pro Tyr Arg Lys Trp
305                 310                 315                 320
Ser Val Ser Glu Ala Ile Ile Lys Tyr Trp Asn His Lys His Lys His
                325                 330                 335
Gly Arg Gly Leu Leu Ser Gly His Gly Gly Leu Lys Ala Arg Met Ile
                340                 345                 350
Glu Gly Ser His His Leu His Ser Arg Ser Val Val Lys Arg Gln Asn
            355                 360                 365
Glu Thr Thr Thr Val Val Met Asp Glu Ser Lys Leu Val Pro Leu Glu
    370                 375                 380
```

| Tyr | Pro | Gly | Ala | Ala | Cys | Gly | Ser | Lys | Pro | Ala | Asp | Leu | Val | Leu | Asp |
| 385 | | | | | 390 | | | | | 395 | | | | | 400 |

| Leu | Thr | Phe | Gly | Leu | Asn | Phe | Ala | Thr | Gly | His | Trp | Met | Ile | Asn | Gly |
| | | | | 405 | | | | | 410 | | | | | 415 | |

| Ile | Pro | Tyr | Glu | Ser | Pro | Lys | Ile | Pro | Thr | Leu | Leu | Lys | Ile | Leu | Thr |
| | | | 420 | | | | | 425 | | | | | 430 | | |

| Asp | Glu | Asp | Gly | Val | Thr | Glu | Ser | Asp | Phe | Thr | Lys | Glu | Glu | His | Thr |
| | | 435 | | | | | 440 | | | | | 445 | | | |

| Val | Ile | Leu | Pro | Lys | Asn | Lys | Cys | Ile | Glu | Phe | Asn | Ile | Lys | Gly | Asn |
| | 450 | | | | | 455 | | | | | 460 | | | | |

| Ser | Gly | Ile | Pro | Ile | Thr | His | Pro | Val | His | Leu | His | Gly | His | Thr | Trp |
| 465 | | | | | 470 | | | | | 475 | | | | | 480 |

| Asp | Val | Val | Gln | Phe | Gly | Asn | Asn | Pro | Pro | Asn | Tyr | Val | Asn | Pro | Pro |
| | | | | 485 | | | | | 490 | | | | | 495 | |

| Arg | Arg | Asp | Val | Val | Gly | Ser | Thr | Asp | Ala | Gly | Val | Arg | Ile | Gln | Phe |
| | | | 500 | | | | | 505 | | | | | 510 | | |

| Lys | Thr | Asp | Asn | Pro | Gly | Pro | Trp | Phe | Leu | His | Cys | His | Ile | Asp | Trp |
| | | 515 | | | | | 520 | | | | | 525 | | | |

| His | Leu | Glu | Glu | Gly | Phe | Ala | Met | Val | Phe | Ala | Glu | Ala | Pro | Glu | Ala |
| | 530 | | | | | 535 | | | | | 540 | | | | |

| Val | Lys | Gly | Gly | Pro | Lys | Ser | Val | Ala | Val | Asp | Ser | Gln | Trp | Glu | Gly |
| 545 | | | | | 550 | | | | | 555 | | | | | 560 |

| Leu | Cys | Gly | Lys | Tyr | Asp | Asn | Trp | Leu | Lys | Ser | Asn | Pro | Gly | Gln | Leu |
| | | | | 565 | | | | | 570 | | | | | 575 | |

( 2 ) INFORMATION FOR SEQ ID NO:3:

( i ) SEQUENCE CHARACTERISTICS:
        ( A ) LENGTH: 3117 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Rhizoctonia laccase ( i x ) FEATURE:
        ( A ) NAME/KEY: CDS
        ( B ) LOCATION: join(393..524, 577..687, 737..799, 860..985,
                1043..1045, 1097..1219, 1269..1538, 1601..1996,
                2047..2118, 2174..2284, 2338..2439, 2495..2635,
                2693..2725, 2786..2899)

( i x ) FEATURE:
        ( A ) NAME/KEY: intron
        ( B ) LOCATION: 525..576

( i x ) FEATURE:
        ( A ) NAME/KEY: intron
        ( B ) LOCATION: 688..736

( i x ) FEATURE:
        ( A ) NAME/KEY: intron
        ( B ) LOCATION: 800..859

( i x ) FEATURE:
        ( A ) NAME/KEY: intron
        ( B ) LOCATION: 986..1042

( i x ) FEATURE:
        ( A ) NAME/KEY: intron
        ( B ) LOCATION: 1220..1268

( i x ) FEATURE:
        ( A ) NAME/KEY: intron (B) LOCATION: 1539..1600

(ix) FEATURE:
(A) NAME/KEY: intron
(B) LOCATION: 1823..1936

(ix) FEATURE:
(A) NAME/KEY: intron
(B) LOCATION: 1973..2046

(ix) FEATURE:
(A) NAME/KEY: intron
(B) LOCATION: 2119..2173

(ix) FEATURE:
(A) NAME/KEY: intron
(B) LOCATION: 2285..2337

(ix) FEATURE:
(A) NAME/KEY: intron
(B) LOCATION: 2440..2494

(ix) FEATURE:
(A) NAME/KEY: intron
(B) LOCATION: 2636..2692

(ix) FEATURE:
(A) NAME/KEY: intron
(B) LOCATION: 1046..1096

(xi) SEQUENCE DESCRIPTION: SEQ ID NO:3:

```
GAGTGATCCG CCAGAGTTCA GGCGGATAAG TTCCTAAATA GTCATTCGCC TATTCGTGTA      60

CCTCAGCATA CTGACGACAT ACCGCCAGAT CGCCCTCGGT TCGGGCGTGG CATACGTTCG     120

CAAGGGCACC TCACGGAGCA AACTCTAAAA AGCTTCGGCA TGGATTGCAT TTTGTATTGT     180

AAACAAGTTA CGAGAAAAAC AATAGATCAG TTTTTGCCGA ATCGGATGGC TTGAAACGGA     240

AGTACCGATG GCCGATCCGA GTCGAATGAA TTAACGCATC TGAAACGGGA CCCTGAGTCG     300

AGGCACCCGC CGGCCTTGGC CGTATAAGTC ACTTGTCGCC AACTAGCACT TTTTCATTCC     360

CCCTTTTCTT CTTCCTCGTC TTCTTCTTCT CT ATG GCT CGG TCG ACT ACT TCA      413
                                    Met Ala Arg Ser Thr Thr Ser
                                     1               5

CTC TTT GCA CTG TCT CTC GTT GCT TCA GCG TTT GCT CGA GTC GTT GAC      461
Leu Phe Ala Leu Ser Leu Val Ala Ser Ala Phe Ala Arg Val Val Asp
         10              15                  20

TAT GGG TTT GAT GTG GCT AAT GGG GCA GTT GCT CCG GAT GGT GTA ACA      509
Tyr Gly Phe Asp Val Ala Asn Gly Ala Val Ala Pro Asp Gly Val Thr
     25              30                  35

AGG AAC GCG GTT CTC GTGAGTTAGC TGTAAGATGG TGTATATGCT GGTTGCCTAA      564
Arg Asn Ala Val Leu
40

CGGGAATGTC AG GTC AAT GGT CGC TTC CCT GGT CCA TTG ATC ACC GCC        612
              Val Asn Gly Arg Phe Pro Gly Pro Leu Ile Thr Ala
                       45                  50                  55

AAC AAG GGG GAT ACA CTT AAA ATC ACC GTG CGG AAT AAA CTC TCC GAT      660
Asn Lys Gly Asp Thr Leu Lys Ile Thr Val Arg Asn Lys Leu Ser Asp
             60              65                  70

CCA ACT ATG CGA AGG AGC ACG ACC ATC GTTAGTACTT CCCCTCATCT            707
Pro Thr Met Arg Arg Ser Thr Thr Ile
         75              80

GTCTTGAAAC TTTCTCATCT TTTTGAAG CAC TGG CAC GGT CTG CTC CAA CAC      760
                                His Trp His Gly Leu Leu Gln His
                                                     85

AGG ACG GCA GAA GAA GAT GGC CCG GCC TTT GTA ACC CAG GTATGCCTTA      809
Arg Thr Ala Glu Glu Asp Gly Pro Ala Phe Val Thr Gln
     90              95                  100
```

```
TCCTATCGCT GCTCTGTCCC CGCGTCCTTC CCTGACTCGG GCGATTCTAG TGC CCG              865
                                                        Cys Pro

ATT CCT CCG CAA GAA TCG TAC ACC TAT ACG ATG CCG CTC GGC GAA CAG              913
Ile Pro Pro Gln Glu Ser Tyr Thr Tyr Thr Met Pro Leu Gly Glu Gln
105             110             115             120

ACC GGC ACG TAT TGG TAC CAC AGC CAC TTG AGC TCC CAG TAT GTG GAC              961
Thr Gly Thr Tyr Trp Tyr His Ser His Leu Ser Ser Gln Tyr Val Asp
                125             130             135

GGG TTG CGT GGG CCC ATC GTT ATT GTAAGTCTTC ATTTAACCTT ATTCTTGGTT            1015
Gly Leu Arg Gly Pro Ile Val Ile
            140

ATGGCTGATT GTGACGTCGT GGTTAGT ATG TTCGTGGCTT CCACAAGAAG                     1065
                              Met
                              145

TCAGCAGCCC TTGAAGCTAA CTTTATTCCA G GAC CCC CAC GAC CCG TAC AGA              1117
                                  Asp Pro His Asp Pro Tyr Arg
                                                  150

AAC TAC TAT GAT GTC GAC GAC GAG CGT ACG GTC TTT ACT TTA GCA GAC             1165
Asn Tyr Tyr Asp Val Asp Asp Glu Arg Thr Val Phe Thr Leu Ala Asp
            155             160             165

TGG TAC CAC ACG CCG TCG GAG GCT ATC ATT GCC ACC CAC GAT GTC TTG             1213
Trp Tyr His Thr Pro Ser Glu Ala Ile Ile Ala Thr His Asp Val Leu
        170             175             180

AAA ACG GTACGCGTTA ATCCTTCTAG CTTTCTTTCC TTGGGTCACT TTCTATCAG              1268
Lys Thr
185

ATC CCC GAC TCG GGT ACG ATC AAC GGC AAA GGC AAA TAC GAT CCT GCT             1316
Ile Pro Asp Ser Gly Thr Ile Asn Gly Lys Gly Lys Tyr Asp Pro Ala
            190             195             200

TCG GCT AAC ACC AAC AAC ACG ACA CTC GAG AAC CTC TAC ACT CTC AAA             1364
Ser Ala Asn Thr Asn Asn Thr Thr Leu Glu Asn Leu Tyr Thr Leu Lys
            205             210             215

GTC AAA CGC GGC AAG CGG TAT CGC CTG AGG ATT ATC AAC GCC TCG GCC             1412
Val Lys Arg Gly Lys Arg Tyr Arg Leu Arg Ile Ile Asn Ala Ser Ala
220             225             230

ATC GCT TCG TTC CGG TTC GGC GTG CAG GGC CAC AAG TGC ACG ATC ATC             1460
Ile Ala Ser Phe Arg Phe Gly Val Gln Gly His Lys Cys Thr Ile Ile
235             240             245             250

GAG GCT GAT GGC GTC CTC ACC AAA CCG ATC GAG GTC GAT GCG TTT GAT             1508
Glu Ala Asp Gly Val Leu Thr Lys Pro Ile Glu Val Asp Ala Phe Asp
                255             260             265

ATT CTA GCA GGC CAG AGG TAT AGC TGC ATC GTAAGTCTAC CTATGCCTTG              1558
Ile Leu Ala Gly Gln Arg Tyr Ser Cys Ile
            270             275

TTGTGGAGAT AAGAACCTGA CTGAATGTAT GCGCTCCAAT AG TTG AAG GCC GAC             1612
                                               Leu Lys Ala Asp
                                                           280

CAA GAT CCT GAT TCC TAC TGG ATA AAT GCG CCA ATC ACA AAC GTT CTC             1660
Gln Asp Pro Asp Ser Tyr Trp Ile Asn Ala Pro Ile Thr Asn Val Leu
            285             290             295

AAC ACC AAC GTC CAG GCA TTG CTA GTG TAT GAA GAT GAC AAG CGT CCT             1708
Asn Thr Asn Val Gln Ala Leu Leu Val Tyr Glu Asp Asp Lys Arg Pro
            300             305             310

ACT CAC TAC CCC TGG AAG CCG TTT TTG ACA TGG AAG ATA TCA AAT GAA             1756
Thr His Tyr Pro Trp Lys Pro Phe Leu Thr Trp Lys Ile Ser Asn Glu
            315             320             325

ATC ATT CAG TAC TGG CAG CAC AAG CAC GGG TCG CAC GGT CAC AAG GGA             1804
Ile Ile Gln Tyr Trp Gln His Lys His Gly Ser His Gly His Lys Gly
            330             335             340
```

| | | | | | | | | | | | | | | | | |
|---|---|---|---|---|---|---|---|---|---|---|---|---|---|---|---|---|
| AAG | GGG | CAT | CAT | CAT | AAA | GTC | CGG | GCC | ATT | GGA | GGT | GTA | TCC | GGG | TTG | 1852 |
| Lys | Gly | His | His | His | Lys | Val | Arg | Ala | Ile | Gly | Gly | Val | Ser | Gly | Leu | |
| 345 | | | | 350 | | | | | 355 | | | | | | 360 | |
| AGC | TCC | AGG | GTT | AAG | AGC | CGG | GCG | AGT | GAC | CTA | TCG | AAG | AAG | GCT | GTC | 1900 |
| Ser | Ser | Arg | Val | Lys | Ser | Arg | Ala | Ser | Asp | Leu | Ser | Lys | Lys | Ala | Val | |
| | | | | 365 | | | | | 370 | | | | | | 375 | |
| GAG | TTG | GCT | GCT | GCA | CTC | GTT | GCG | GGT | GAG | GCC | GAG | TTG | GAC | AAG | AGG | 1948 |
| Glu | Leu | Ala | Ala | Ala | Leu | Val | Ala | Gly | Glu | Ala | Glu | Leu | Asp | Lys | Arg | |
| | | | 380 | | | | | 385 | | | | | 390 | | | |
| CAG | AAT | GAG | GAT | AAT | TCG | ACT | ATT | GTA | TTG | GAT | GAG | ACC | AAG | CTT | ATT | 1996 |
| Gln | Asn | Glu | Asp | Asn | Ser | Thr | Ile | Val | Leu | Asp | Glu | Thr | Lys | Leu | Ile | |
| | | | 395 | | | | | 400 | | | | | 405 | | | |

GTAAGTCCCT TAATTTTTTT CGGTGTCACG GAAGCTAACC CGCGTAATAG CCG TTG     2052
                                                       Pro Leu
                                                           410

| | | | | | | | | | | | | | | | | |
|---|---|---|---|---|---|---|---|---|---|---|---|---|---|---|---|---|
| GTT | CAA | CCT | GGT | GCA | CCG | GGC | GGC | TCC | AGA | CCA | GCT | GAC | GTC | GTG | GTC | 2100 |
| Val | Gln | Pro | Gly | Ala | Pro | Gly | Gly | Ser | Arg | Pro | Ala | Asp | Val | Val | Val | |
| | | | | 415 | | | | | 420 | | | | | 425 | | |
| CCT | CTG | GAC | TTT | GGC | CTC | GTATGTGGCT | | TCTTGTTATT | | CGTCCGGAAT | | | | | | 2148 |
| Pro | Leu | Asp | Phe | Gly | Leu | | | | | | | | | | | |
| | | | 430 | | | | | | | | | | | | | |

GCAAACTGAT TGGGTGGGC TATAG AAC TTT GCC AAC GGA CTG TGG ACG ATA     2200
                            Asn Phe Ala Asn Gly Leu Trp Thr Ile
                            435                         440

| | | | | | | | | | | | | | | | | |
|---|---|---|---|---|---|---|---|---|---|---|---|---|---|---|---|---|
| AAC | AAT | GTC | TCC | TAC | TCC | CCT | CCG | GAT | GTC | CCT | ACT | CTC | CTC | AAG | ATC | 2248 |
| Asn | Asn | Val | Ser | Tyr | Ser | Pro | Pro | Asp | Val | Pro | Thr | Leu | Leu | Lys | Ile | |
| | | | 445 | | | | | 450 | | | | | 455 | | | |
| TTG | ACC | GAC | AAA | GAC | AAA | GTC | GAC | GCT | TCT | GAC | TTC | GTAGGTCCT | | | | 2294 |
| Leu | Thr | Asp | Lys | Asp | Lys | Val | Asp | Ala | Ser | Asp | Phe | | | | | |
| | | 460 | | | | | 465 | | | | | | | | | |

CTTCTTCTTT TCAAACTAGC TACTGACATT AAGTGAACGT CAG ACG GCC GAT GAA    2349
                                              Thr Ala Asp Glu
                                                  470

| | | | | | | | | | | | | | | | | |
|---|---|---|---|---|---|---|---|---|---|---|---|---|---|---|---|---|
| CAC | ACG | TAT | ATT | CTT | CCA | AAG | AAC | CAA | GTT | GTC | GAG | TTG | CAC | ATC | AAG | 2397 |
| His | Thr | Tyr | Ile | Leu | Pro | Lys | Asn | Gln | Val | Val | Glu | Leu | His | Ile | Lys | |
| | 475 | | | | | 480 | | | | | 485 | | | | | |
| GGA | CAG | GCT | TTG | GGA | ATC | GTA | CAC | CCC | CTT | CAT | CTG | CAT | GGC | | | 2439 |
| Gly | Gln | Ala | Leu | Gly | Ile | Val | His | Pro | Leu | His | Leu | His | Gly | | | |
| 490 | | | | | 495 | | | | | 500 | | | | | | |

GTACGTCTTT CTCACACTGT CCAGCTCCT ATTCTCTAAC ACACTCCTGC GATAG CAT    2497
                                                             His

| | | | | | | | | | | | | | | | | |
|---|---|---|---|---|---|---|---|---|---|---|---|---|---|---|---|---|
| GCG | TTC | GAC | GTC | GTC | CAA | TTC | GGC | GAC | AAC | GCT | CCA | AAC | TAC | GTG | AAC | 2545 |
| Ala | Phe | Asp | Val | Val | Gln | Phe | Gly | Asp | Asn | Ala | Pro | Asn | Tyr | Val | Asn | |
| 505 | | | | 510 | | | | | 515 | | | | | 520 | | |
| CCT | CCG | CGT | AGG | GAT | GTA | GTA | GGC | GTA | ACT | GAT | GCT | GGA | GTC | CGT | ATC | 2593 |
| Pro | Pro | Arg | Arg | Asp | Val | Val | Gly | Val | Thr | Asp | Ala | Gly | Val | Arg | Ile | |
| | | | 525 | | | | | 530 | | | | | 535 | | | |
| CAG | TTC | AGA | ACC | GAT | AAC | CCG | GGC | CCT | TGG | TTC | CTC | CAT | TGC | | | 2635 |
| Gln | Phe | Arg | Thr | Asp | Asn | Pro | Gly | Pro | Trp | Phe | Leu | His | Cys | | | |
| | | | 540 | | | | | 545 | | | | | 550 | | | |

GTATGCTCTT CATCTCCCAC CGCTTGTTCT TTACTTATGG TTTACCTTGC GATTTAG     2692

| | | | | | | | | | | | | | | | | |
|---|---|---|---|---|---|---|---|---|---|---|---|---|---|---|---|---|
| CAC | ATT | GAT | TGG | CAC | TTG | GAA | GAA | GGA | TTT | GCT | GTAAGTTATT | | ATTCCTATTC | | | 2745 |
| His | Ile | Asp | Trp | His | Leu | Glu | Glu | Gly | Phe | Ala | | | | | | |
| | | | 555 | | | | | 560 | | | | | | | | |

CGAAGCATCG GGGAGATGCT AACCAAGGGT GTGTTTTAAG ATG GTA TTC GCC GAA    2800
                                             Met Val Phe Ala Glu
                                                             565

| | | | | | | | | | | | | | | | | |
|---|---|---|---|---|---|---|---|---|---|---|---|---|---|---|---|---|
| GCG | CCT | GAA | GAT | ATC | AAG | AAA | GGC | TCT | CAG | AGT | GTC | AAG | CCT | GAC | GGA | 2848 |

|   |   |   |   |   |   |   |   |   |   |   |   |   |   |   |   |   |
|---|---|---|---|---|---|---|---|---|---|---|---|---|---|---|---|---|
| Ala | Pro | Glu | Asp<br>570 | Ile | Lys | Lys | Gly | Ser<br>575 | Gln | Ser | Val | Lys | Pro<br>580 | Asp | Gly |   |

| CAA | TGG | AAG | AAA | CTA | TGC | GAG | AAG | TAT | GAG | AAG | TTG | CCT | GAA | GCA | CTG | 2896 |
|-----|-----|-----|-----|-----|-----|-----|-----|-----|-----|-----|-----|-----|-----|-----|-----|------|
| Gln | Trp | Lys<br>585 | Lys | Leu | Cys | Glu | Lys<br>590 | Tyr | Glu | Lys | Leu | Pro<br>595 | Glu | Ala | Leu |   |

| CAG | TGAAGTTGCA | GTTGTTTCCC | ATTCGGGAAC | TGGCTCACTA | TTCCTTTTGC | 2949 |
|-----|------------|------------|------------|------------|------------|------|
| Gln |            |            |            |            |            |      |

ATAATTCGGA CTTTTATTTT GGGACATTAT TGGACTATGG ACTTGTTTGT CACACCCTCG    3009

CTCACTGTGT CCCTCGTTGA GTACCTATAC TCTATTCGTA TAGTGGGAAT ATGGAATATC    3069

GGATGTAATA AATGCTCGTG CGTTTGGTGC TCGAAATGGG GTAGGACT    3117

(2) INFORMATION FOR SEQ ID NO:4:

(i) SEQUENCE CHARACTERISTICS:
    (A) LENGTH: 599 amino acids
    (B) TYPE: amino acid
    (D) TOPOLOGY: linear (ii) MOLECULE TYPE: protein (xi) SEQUENCE DESCRIPTION: SEQ ID NO:4:

| Met<br>1 | Ala | Arg | Ser | Thr<br>5 | Thr | Ser | Leu | Phe | Ala<br>10 | Leu | Ser | Leu | Val | Ala<br>15 | Ser |
|----|----|----|----|----|----|----|----|----|----|----|----|----|----|----|----|
| Ala | Phe | Ala | Arg<br>20 | Val | Val | Asp | Tyr | Gly<br>25 | Phe | Asp | Val | Ala | Asn<br>30 | Gly | Ala |
| Val | Ala | Pro<br>35 | Asp | Gly | Val | Thr | Arg<br>40 | Asn | Ala | Val | Leu | Val<br>45 | Asn | Gly | Arg |
| Phe | Pro<br>50 | Gly | Pro | Leu | Ile | Thr<br>55 | Ala | Asn | Lys | Gly | Asp<br>60 | Thr | Leu | Lys | Ile |
| Thr<br>65 | Val | Arg | Asn | Lys | Leu<br>70 | Ser | Asp | Pro | Thr | Met<br>75 | Arg | Arg | Ser | Thr | Thr<br>80 |
| Ile | His | Trp | His | Gly<br>85 | Leu | Leu | Gln | His | Arg<br>90 | Thr | Ala | Glu | Glu | Asp<br>95 | Gly |
| Pro | Ala | Phe | Val<br>100 | Thr | Gln | Cys | Pro | Ile<br>105 | Pro | Pro | Gln | Glu | Ser<br>110 | Tyr | Thr |
| Tyr | Thr | Met<br>115 | Pro | Leu | Gly | Glu | Gln<br>120 | Thr | Gly | Thr | Tyr | Trp<br>125 | Tyr | His | Ser |
| His | Leu<br>130 | Ser | Ser | Gln | Tyr | Val<br>135 | Asp | Gly | Leu | Arg | Gly<br>140 | Pro | Ile | Val | Ile |
| Met<br>145 | Asp | Pro | His | Asp | Pro<br>150 | Tyr | Arg | Asn | Tyr | Tyr<br>155 | Asp | Val | Asp | Asp | Glu<br>160 |
| Arg | Thr | Val | Phe | Thr<br>165 | Leu | Ala | Asp | Trp | Tyr<br>170 | His | Thr | Pro | Ser | Glu<br>175 | Ala |
| Ile | Ile | Ala | Thr | His | Asp | Val | Leu | Lys | Thr | Ile | Pro | Asp | Ser | Gly | Thr |
|  |  |  | 180 |  |  |  |  | 185 |  |  |  |  | 190 |  |  |
| Ile | Asn | Gly<br>195 | Lys | Gly | Lys | Tyr | Asp<br>200 | Pro | Ala | Ser | Ala | Asn<br>205 | Thr | Asn | Asn |
| Thr | Thr<br>210 | Leu | Glu | Asn | Leu | Tyr<br>215 | Thr | Leu | Lys | Val | Lys<br>220 | Arg | Gly | Lys | Arg |
| Tyr<br>225 | Arg | Leu | Arg | Ile | Ile<br>230 | Asn | Ala | Ser | Ala | Ile<br>235 | Ala | Ser | Phe | Arg | Phe<br>240 |
| Gly | Val | Gln | Gly | His<br>245 | Lys | Cys | Thr | Ile | Ile<br>250 | Glu | Ala | Asp | Gly | Val<br>255 | Leu |
| Thr | Lys | Pro | Ile<br>260 | Glu | Val | Asp | Ala | Phe<br>265 | Asp | Ile | Leu | Ala | Gly<br>270 | Gln | Arg |

```
Tyr  Ser  Cys  Ile  Leu  Lys  Ala  Asp  Gln  Asp  Pro  Asp  Ser  Tyr  Trp  Ile
          275                280                285

Asn  Ala  Pro  Ile  Thr  Asn  Val  Leu  Asn  Thr  Asn  Val  Gln  Ala  Leu  Leu
     290                295                300

Val  Tyr  Glu  Asp  Asp  Lys  Arg  Pro  Thr  His  Tyr  Pro  Trp  Lys  Pro  Phe
305                 310                315                               320

Leu  Thr  Trp  Lys  Ile  Ser  Asn  Glu  Ile  Ile  Gln  Tyr  Trp  Gln  His  Lys
               325                     330                          335

His  Gly  Ser  His  Gly  His  Lys  Gly  Lys  Gly  His  His  His  Lys  Val  Arg
               340                345                     350

Ala  Ile  Gly  Gly  Val  Ser  Gly  Leu  Ser  Ser  Arg  Val  Lys  Ser  Arg  Ala
          355                     360                     365

Ser  Asp  Leu  Ser  Lys  Lys  Ala  Val  Glu  Leu  Ala  Ala  Ala  Leu  Val  Ala
     370                375                     380

Gly  Glu  Ala  Glu  Leu  Asp  Lys  Arg  Gln  Asn  Glu  Asp  Asn  Ser  Thr  Ile
385                     390                395                          400

Val  Leu  Asp  Glu  Thr  Lys  Leu  Ile  Pro  Leu  Val  Gln  Pro  Gly  Ala  Pro
               405                     410                     415

Gly  Gly  Ser  Arg  Pro  Ala  Asp  Val  Val  Val  Pro  Leu  Asp  Phe  Gly  Leu
          420                     425                     430

Asn  Phe  Ala  Asn  Gly  Leu  Trp  Thr  Ile  Asn  Asn  Val  Ser  Tyr  Ser  Pro
          435                     440                     445

Pro  Asp  Val  Pro  Thr  Leu  Leu  Lys  Ile  Leu  Thr  Asp  Lys  Asp  Lys  Val
     450                     455                460

Asp  Ala  Ser  Asp  Phe  Thr  Ala  Asp  Glu  His  Thr  Tyr  Ile  Leu  Pro  Lys
465                      470                475                          480

Asn  Gln  Val  Val  Glu  Leu  His  Ile  Lys  Gly  Gln  Ala  Leu  Gly  Ile  Val
               485                     490                          495

His  Pro  Leu  His  Leu  His  Gly  His  Ala  Phe  Asp  Val  Val  Gln  Phe  Gly
               500                     505                     510

Asp  Asn  Ala  Pro  Asn  Tyr  Val  Asn  Pro  Pro  Arg  Arg  Asp  Val  Val  Gly
          515                     520                     525

Val  Thr  Asp  Ala  Gly  Val  Arg  Ile  Gln  Phe  Arg  Thr  Asp  Asn  Pro  Gly
530                      535                     540

Pro  Trp  Phe  Leu  His  Cys  His  Ile  Asp  Trp  His  Leu  Glu  Glu  Gly  Phe
545                      550                     555                      560

Ala  Met  Val  Phe  Ala  Glu  Ala  Pro  Glu  Asp  Ile  Lys  Lys  Gly  Ser  Gln
               565                     570                     575

Ser  Val  Lys  Pro  Asp  Gly  Gln  Trp  Lys  Lys  Leu  Cys  Glu  Lys  Tyr  Glu
               580                     585                     590

Lys  Leu  Pro  Glu  Ala  Leu  Gln
               595
```

( 2 ) INFORMATION FOR SEQ ID NO:5:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Ala  Val  Arg  Asn  Tyr  Lys  Phe  Asp  Ile  Lys  Asn  Val  Asn  Val  Ala  Pro
1               5                       10                          15

Asp  Gly  Phe  Gln  Arg  Pro  Ile  Val  Ser  Val
```

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Ser Gln Tyr Val Asp Gly Leu Arg Gly Pro Leu Val Ile Tyr Asp Pro
 1               5                  10                  15
Asp Asp Asp His
            20
```

( 2 ) INFORMATION FOR SEQ ID NO:7:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Ser Arg Tyr Asx Val Asx Asx Ala Ser Thr Val Val Met Leu Glu Asx
 1               5                  10                  15
Trp Tyr Arg Thr Pro Ala Xaa Val Leu Glu
            20                  25
```

( 2 ) INFORMATION FOR SEQ ID NO:8:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Ser Leu Gly Pro Thr Pro Asn Tyr Val Asn Pro Xaa Ile Arg Asp Val
 1               5                  10                  15
Val Arg Val Gly Gly Thr Thr Val Val
            20                  25
```

( 2 ) INFORMATION FOR SEQ ID NO:9:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Gly Leu Ala Leu Val Phe Ala Glu Ala Pro Ser Gln Ile Arg Gln Gly
 1               5                  10                  15
Val Gln Ser Val Gln Pro Asp Asp Ala
            20                  25
```

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Ile Arg Tyr Val Gly Gly Pro Ala Val Xaa Arg Ser Val Ile
1               5                   10
```

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Ile Leu Ala Asn Pro Ala
1               5
```

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Tyr Glu Ala Pro Ser Leu Pro Thr
1               5
```

( 2 ) INFORMATION FOR SEQ ID NO:13:

( i ) SEQUENCE CHARACTERISTICS:
        ( A ) LENGTH: 1672 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Rhizoctonia laccase ( i x ) FEATURE:
        ( A ) NAME/KEY: CDS
        ( B ) LOCATION: 85..1671

( x i ) SEQUENCE DESCRIPTION: SEQ ID NO:13:

```
CTAACGCTTG GTGCCGAGCT CGGATCCACT AGTAACGCGC GCCAGTGTGC TGGAATTCGC      60

GGCCGCGTCG ACACCTCCTT CAAG ATG CTT TCT AGC ATT ACC CTC CTA CCT         111
                          Met Leu Ser Ser Ile Thr Leu Leu Pro
                            1               5

TTG CTC GCT GCG GTC TCA ACC CCC GCC TTT GCT GCC GTC CGC AAC TAT        159
Leu Leu Ala Ala Val Ser Thr Pro Ala Phe Ala Ala Val Arg Asn Tyr
 10              15                  20                  25

AAG TTC GAC ATC AAG AAC GTC AAT GTC GCT CCC GAT GGC TTT CAG CGC        207
Lys Phe Asp Ile Lys Asn Val Asn Val Ala Pro Asp Gly Phe Gln Arg
```

|  |  |  |  |  |  |  |  |  |  |  |  |  |  |  |  |  |
|---|---|---|---|---|---|---|---|---|---|---|---|---|---|---|---|---|
| TCT | ATC | GTC | TCC | GTC | AAC | GGT | TTA | GTT | CCT | GGC | ACG | TTG | ATC | ACG | GCC | 255 |
| Ser | Ile | Val | Ser<br>45 | Val | Asn | Gly | Leu | Val<br>50 | Pro | Gly | Thr | Leu | Ile<br>55 | Thr | Ala | |
| AAC | AAG | GGT | GAC | ACC | TTG | CGC | ATT | AAT | GTC | ACG | AAT | CAA | CTC | ACG | GAC | 303 |
| Asn | Lys | Gly<br>60 | Asp | Thr | Leu | Arg | Ile<br>65 | Asn | Val | Thr | Asn | Gln<br>70 | Leu | Thr | Asp | |
| CCT | AGT | ATG | CGT | CGT | GCC | ACA | ACG | ATT | CAT | TGG | CAT | GGA | TTG | TTC | CAA | 351 |
| Pro | Ser<br>75 | Met | Arg | Arg | Ala | Thr | Thr<br>80 | Ile | His | Trp | His<br>85 | Gly | Leu | Phe | Gln | |
| GCT | ACT | ACC | GCC | GAC | GAG | GAT | GGC | CCC | GCA | TTC | GTC | ACG | CAA | TGC | CCT | 399 |
| Ala<br>90 | Thr | Thr | Ala | Asp | Glu<br>95 | Asp | Gly | Pro | Ala | Phe<br>100 | Val | Thr | Gln | Cys | Pro<br>105 | |
| ATT | GCG | CAA | AAT | TTG | TCC | TAT | ACA | TAC | GAG | ATC | CCA | TTG | CGC | GGC | CAA | 447 |
| Ile | Ala | Gln | Asn | Leu<br>110 | Ser | Tyr | Thr | Tyr | Glu<br>115 | Ile | Pro | Leu | Arg | Gly<br>120 | Gln | |
| ACA | GGA | ACC | ATG | TGG | TAT | CAC | GCC | CAT | CTT | GCG | AGT | CAA | TAT | GTC | GAT | 495 |
| Thr | Gly | Thr | Met<br>125 | Trp | Tyr | His | Ala | His<br>130 | Leu | Ala | Ser | Gln | Tyr<br>135 | Val | Asp | |
| GGA | TTG | CGA | GGC | CCT | TTG | GTC | ATC | TAT | GAT | CCA | AAC | GAC | CCA | CAC | AAG | 543 |
| Gly | Leu | Arg<br>140 | Gly | Pro | Leu | Val | Ile<br>145 | Tyr | Asp | Pro | Asn | Asp<br>150 | Pro | His | Lys | |
| TCG | CGC | TAC | GAC | GTG | GAT | GAT | GCG | AGC | ACA | GTA | GTC | ATG | CTT | GAG | GAC | 591 |
| Ser | Arg<br>155 | Tyr | Asp | Val | Asp | Asp<br>160 | Ala | Ser | Thr | Val | Val<br>165 | Met | Leu | Glu | Asp | |
| TGG | TAC | CAT | ACT | CCG | GCA | CCC | GTT | CTA | GAA | AAG | CAA | ATG | TTC | TCG | ACT | 639 |
| Trp<br>170 | Tyr | His | Thr | Pro | Ala<br>175 | Pro | Val | Leu | Glu | Lys<br>180 | Gln | Met | Phe | Ser | Thr<br>185 | |
| AAT | AAC | ACC | GCT | CTG | CTC | TCT | CCT | GTT | CCG | GAC | TCG | GGT | CTT | ATC | AAT | 687 |
| Asn | Asn | Thr | Ala | Leu<br>190 | Leu | Ser | Pro | Val | Pro<br>195 | Asp | Ser | Gly | Leu | Ile<br>200 | Asn | |
| GGC | AAA | GGG | CGC | TAT | GTG | GGC | GGT | CCC | GCA | GTT | CCC | CGG | TCA | GTA | ATC | 735 |
| Gly | Lys | Gly | Arg<br>205 | Tyr | Val | Gly | Gly | Pro<br>210 | Ala | Val | Pro | Arg | Ser<br>215 | Val | Ile | |
| AAC | GTA | AAA | CGT | GGG | AAA | CGA | TAT | CGC | TTG | CGC | GTA | ATC | AAC | GCT | TCT | 783 |
| Asn | Val | Lys<br>220 | Arg | Gly | Lys | Arg | Tyr<br>225 | Arg | Leu | Arg | Val | Ile<br>230 | Asn | Ala | Ser | |
| GCT | ATC | GGG | TCG | TTT | ACC | TTT | TCG | ATC | GAA | GGA | CAT | AGT | CTG | ACT | GTC | 831 |
| Ala | Ile<br>235 | Gly | Ser | Phe | Thr | Phe<br>240 | Ser | Ile | Glu | Gly | His<br>245 | Ser | Leu | Thr | Val | |
| ATT | GAG | GCC | GAT | GGG | ATC | CTG | CAC | CAG | CCC | TTG | GCT | GTT | GAC | AGC | TTC | 879 |
| Ile<br>250 | Glu | Ala | Asp | Gly | Ile<br>255 | Leu | His | Gln | Pro | Leu<br>260 | Ala | Val | Asp | Ser | Phe<br>265 | |
| CAG | ATT | TAC | GCT | GGA | CAA | CGC | TAC | TCT | GTC | ATC | GTT | GAA | GCC | AAC | CAA | 927 |
| Gln | Ile | Tyr | Ala | Gly<br>270 | Gln | Arg | Tyr | Ser | Val<br>275 | Ile | Val | Glu | Ala | Asn<br>280 | Gln | |
| ACC | GCC | GCC | AAC | TAC | TGG | ATT | CGT | GCA | CCA | ATG | ACC | GTT | GCA | GGA | GCC | 975 |
| Thr | Ala | Ala | Asn<br>285 | Tyr | Trp | Ile | Arg | Ala<br>290 | Pro | Met | Thr | Val | Ala<br>295 | Gly | Ala | |
| GGA | ACC | AAT | GCA | AAC | TTG | GAC | CCC | ACC | AAT | GTC | TTT | GCC | GTA | TTG | CAC | 1023 |
| Gly | Thr | Asn<br>300 | Ala | Asn | Leu | Asp | Pro<br>305 | Thr | Asn | Val | Phe | Ala<br>310 | Val | Leu | His | |
| TAC | GAG | GGA | GCG | CCC | AAC | GCC | GAA | CCC | ACG | ACG | GAA | CAA | GGC | AGT | GCT | 1071 |
| Tyr | Glu<br>315 | Gly | Ala | Pro | Asn | Ala<br>320 | Glu | Pro | Thr | Thr | Glu<br>325 | Gln | Gly | Ser | Ala | |
| ATC | GGT | ACT | GCA | CTC | GTT | GAA | GAG | AAC | CTC | CAT | GCG | CTC | ATC | AAC | CCT | 1119 |
| Ile<br>330 | Gly | Thr | Ala | Leu | Val<br>335 | Glu | Glu | Asn | Leu | His<br>340 | Ala | Leu | Ile | Asn | Pro<br>345 | |
| GGC | GCT | CCG | GGC | GGC | TCC | GCT | CCC | GCA | GAC | GTT | TCC | CTC | AAT | CTT | GCA | 1167 |

| | | | | | | | | | | | | | | |
|---|---|---|---|---|---|---|---|---|---|---|---|---|---|---|
| Gly | Ala | Pro | Gly | Gly 350 | Ser | Ala | Pro | Ala | Asp 355 | Val | Ser | Leu | Asn | Leu 360 | Ala |

| | | | | | | | | | | | | | | | |
|---|---|---|---|---|---|---|---|---|---|---|---|---|---|---|---|
| ATT | GGG | CGC | AGC | ACA | GTT | GAT | GGG | ATT | CTT | AGG | TTC | ACA | TTT | AAT | AAC | 1215
| Ile | Gly | Arg | Ser 365 | Thr | Val | Asp | Gly | Ile 370 | Leu | Arg | Phe | Thr | Phe 375 | Asn | Asn |

| ATC | AAG | TAC | GAG | GCT | CCT | TCG | TTG | CCC | ACG | CTC | TTG | AAG | ATT | TTG | GCA | 1263
|---|---|---|---|---|---|---|---|---|---|---|---|---|---|---|---|---|
| Ile | Lys | Tyr 380 | Glu | Ala | Pro | Ser | Leu 385 | Pro | Thr | Leu | Leu | Lys 390 | Ile | Leu | Ala |

| AAC | AAT | GCG | AGC | AAT | GAC | GCC | GAT | TTC | ACG | CCA | AAT | GAG | CAC | ACT | ATC | 1311
|---|---|---|---|---|---|---|---|---|---|---|---|---|---|---|---|---|
| Asn | Asn 395 | Ala | Ser | Asn | Asp | Ala 400 | Asp | Phe | Thr | Pro | Asn | Glu 405 | His | Thr | Ile |

| GTA | TTG | CCA | CAC | AAT | AAA | GTT | ATC | GAG | CTC | AAT | ATC | ACC | GGA | GGT | GCA | 1359
|---|---|---|---|---|---|---|---|---|---|---|---|---|---|---|---|---|
| Val 410 | Leu | Pro | His | Asn | Lys 415 | Val | Ile | Glu | Leu | Asn 420 | Ile | Thr | Gly | Gly | Ala 425 |

| GAC | CAC | CCT | ATC | CAT | CTC | CAC | GGC | CAT | GTG | TTT | GAT | ATC | GTC | AAA | TCA | 1407
|---|---|---|---|---|---|---|---|---|---|---|---|---|---|---|---|---|
| Asp | His | Pro | Ile | His 430 | Leu | His | Gly | His | Val 435 | Phe | Asp | Ile | Val | Lys 440 | Ser |

| CTC | GGT | GGT | ACC | CCG | AAC | TAT | GTC | AAC | CCG | CCA | CGC | AGG | GAC | GTA | GTT | 1455
|---|---|---|---|---|---|---|---|---|---|---|---|---|---|---|---|---|
| Leu | Gly | Gly | Thr 445 | Pro | Asn | Tyr | Val | Asn 450 | Pro | Pro | Arg | Arg | Asp 455 | Val | Val |

| CGT | GTC | GGA | GGC | ACC | GGT | GTG | GTA | CTC | CGA | TTC | AAG | ACC | GAT | AAC | CCA | 1503
|---|---|---|---|---|---|---|---|---|---|---|---|---|---|---|---|---|
| Arg | Val | Gly 460 | Gly | Thr | Gly | Val | Val 465 | Leu | Arg | Phe | Lys | Thr 470 | Asp | Asn | Pro |

| GGC | CCA | TGG | TTT | GTT | CAC | TGC | CAC | ATT | GAC | TGG | CAC | TTG | GAG | GCT | GGG | 1551
|---|---|---|---|---|---|---|---|---|---|---|---|---|---|---|---|---|
| Gly | Pro 475 | Trp | Phe | Val | His | Cys 480 | His | Ile | Asp | Trp | His 485 | Leu | Glu | Ala | Gly |

| CTC | GCA | CTT | GTC | TTT | GCC | GAG | GCC | CCC | AGC | CAG | ATT | CGC | CAG | GGT | GTC | 1599
|---|---|---|---|---|---|---|---|---|---|---|---|---|---|---|---|---|
| Leu 490 | Ala | Leu | Val | Phe | Ala 495 | Glu | Ala | Pro | Ser | Gln 500 | Ile | Arg | Gln | Gly | Val 505 |

| CAG | TCG | GTC | CAG | CCC | AAC | AAT | GCC | TGG | AAC | CAG | CTC | TGC | CCC | AAG | TAC | 1647
|---|---|---|---|---|---|---|---|---|---|---|---|---|---|---|---|---|
| Gln | Ser | Val | Gln | Pro 510 | Asn | Asn | Ala | Trp | Asn 515 | Gln | Leu | Cys | Pro | Lys 520 | Tyr |

| GCG | GCT | CTT | CCT | CCC | GAT | TTG | CAG | T | | | | | | | | 1672
|---|---|---|---|---|---|---|---|---|---|---|---|---|---|---|---|---|
| Ala | Ala | Leu | Pro 525 | Pro | Asp | Leu | Gln | | | | | | | | |

( 2 ) INFORMATION FOR SEQ ID NO:14:

( i ) SEQUENCE CHARACTERISTICS:
        ( A ) LENGTH: 529 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| Met 1 | Leu | Ser | Ser | Ile 5 | Thr | Leu | Leu | Pro | Leu 10 | Leu | Ala | Ala | Val | Ser 15 | Thr |
|---|---|---|---|---|---|---|---|---|---|---|---|---|---|---|---|
| Pro | Ala | Phe | Ala 20 | Ala | Val | Arg | Asn | Tyr 25 | Lys | Phe | Asp | Ile | Lys 30 | Asn | Val |
| Asn | Val | Ala 35 | Pro | Asp | Gly | Phe | Gln 40 | Arg | Ser | Ile | Val | Ser 45 | Val | Asn | Gly |
| Leu | Val 50 | Pro | Gly | Thr | Leu | Ile 55 | Thr | Ala | Asn | Lys | Gly 60 | Asp | Thr | Leu | Arg |
| Ile 65 | Asn | Val | Thr | Asn | Gln 70 | Leu | Thr | Asp | Pro | Ser 75 | Met | Arg | Arg | Ala | Thr 80 |
| Thr | Ile | His | Trp | His 85 | Gly | Leu | Phe | Gln | Ala 90 | Thr | Thr | Ala | Asp | Glu 95 | Asp |
| Gly | Pro | Ala | Phe 100 | Val | Thr | Gln | Cys | Pro 105 | Ile | Ala | Gln | Asn | Leu 110 | Ser | Tyr |

```
Thr  Tyr  Glu  Ile  Pro  Leu  Arg  Gly  Gln  Thr  Gly  Thr  Met  Trp  Tyr  His
          115                 120                      125

Ala  His  Leu  Ala  Ser  Gln  Tyr  Val  Asp  Gly  Leu  Arg  Gly  Pro  Leu  Val
     130                 135                 140

Ile  Tyr  Asp  Pro  Asn  Asp  Pro  His  Lys  Ser  Arg  Tyr  Asp  Val  Asp  Asp
145                 150                      155                           160

Ala  Ser  Thr  Val  Val  Met  Leu  Glu  Asp  Trp  Tyr  His  Thr  Pro  Ala  Pro
               165                 170                      175

Val  Leu  Glu  Lys  Gln  Met  Phe  Ser  Thr  Asn  Asn  Thr  Ala  Leu  Leu  Ser
          180                 185                           190

Pro  Val  Pro  Asp  Ser  Gly  Leu  Ile  Asn  Gly  Lys  Gly  Arg  Tyr  Val  Gly
          195                 200                      205

Gly  Pro  Ala  Val  Pro  Arg  Ser  Val  Ile  Asn  Val  Lys  Arg  Gly  Lys  Arg
     210                 215                      220

Tyr  Arg  Leu  Arg  Val  Ile  Asn  Ala  Ser  Ala  Ile  Gly  Ser  Phe  Thr  Phe
225                      230                 235                           240

Ser  Ile  Glu  Gly  His  Ser  Leu  Thr  Val  Ile  Glu  Ala  Asp  Gly  Ile  Leu
               245                      250                      255

His  Gln  Pro  Leu  Ala  Val  Asp  Ser  Phe  Gln  Ile  Tyr  Ala  Gly  Gln  Arg
          260                      265                      270

Tyr  Ser  Val  Ile  Val  Glu  Ala  Asn  Gln  Thr  Ala  Ala  Asn  Tyr  Trp  Ile
          275                      280                      285

Arg  Ala  Pro  Met  Thr  Val  Ala  Gly  Ala  Gly  Thr  Asn  Ala  Asn  Leu  Asp
290                           295                      300

Pro  Thr  Asn  Val  Phe  Ala  Val  Leu  His  Tyr  Glu  Gly  Ala  Pro  Asn  Ala
305                      310                 315                           320

Glu  Pro  Thr  Thr  Glu  Gln  Gly  Ser  Ala  Ile  Gly  Thr  Ala  Leu  Val  Glu
               325                      330                      335

Glu  Asn  Leu  His  Ala  Leu  Ile  Asn  Pro  Gly  Ala  Pro  Gly  Gly  Ser  Ala
               340                      345                 350

Pro  Ala  Asp  Val  Ser  Leu  Asn  Leu  Ala  Ile  Gly  Arg  Ser  Thr  Val  Asp
          355                      360                 365

Gly  Ile  Leu  Arg  Phe  Thr  Phe  Asn  Asn  Ile  Lys  Tyr  Glu  Ala  Pro  Ser
370                      375                      380

Leu  Pro  Thr  Leu  Leu  Lys  Ile  Leu  Ala  Asn  Asn  Ala  Ser  Asn  Asp  Ala
385                 390                      395                           400

Asp  Phe  Thr  Pro  Asn  Glu  His  Thr  Ile  Val  Leu  Pro  His  Asn  Lys  Val
               405                      410                      415

Ile  Glu  Leu  Asn  Ile  Thr  Gly  Gly  Ala  Asp  His  Pro  Ile  His  Leu  His
               420                 425                      430

Gly  His  Val  Phe  Asp  Ile  Val  Lys  Ser  Leu  Gly  Gly  Thr  Pro  Asn  Tyr
          435                 440                      445

Val  Asn  Pro  Pro  Arg  Arg  Asp  Val  Val  Arg  Val  Gly  Gly  Thr  Gly  Val
     450                 455                 460

Val  Leu  Arg  Phe  Lys  Thr  Asp  Asn  Pro  Gly  Pro  Trp  Phe  Val  His  Cys
465                      470                 475                           480

His  Ile  Asp  Trp  His  Leu  Glu  Ala  Gly  Leu  Ala  Leu  Val  Phe  Ala  Glu
                    485                 490                      495

Ala  Pro  Ser  Gln  Ile  Arg  Gln  Gly  Val  Gln  Ser  Val  Gln  Pro  Asn  Asn
               500                 505                      510

Ala  Trp  Asn  Gln  Leu  Cys  Pro  Lys  Tyr  Ala  Ala  Leu  Pro  Pro  Asp  Leu
     515                 520                      525
```

Gln